US011497519B2

(12) United States Patent
Madan et al.

(10) Patent No.: US 11,497,519 B2
(45) Date of Patent: Nov. 15, 2022

(54) ULTRASONIC SURGICAL INSTRUMENT BLADE WITH HEAT REDUCTION FEATURE

(71) Applicant: Ethicon LLC, Guaynabo, PR (US)

(72) Inventors: Ashvani K. Madan, Mason, OH (US); David A. Witt, Maineville, OH (US); John A. Weed, III, Monroe, OH (US); Stephen J. Balek, Springboro, OH (US); Joseph Isosaki, Cincinnati, OH (US); Peter K. Shires, Hamilton, OH (US); William D. Dannaher, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/835,626

(22) Filed: Mar. 31, 2020

(65) Prior Publication Data

US 2020/0315651 A1 Oct. 8, 2020

Related U.S. Application Data

(63) Continuation of application No. 15/163,830, filed on May 25, 2016, now Pat. No. 10,660,663.

(51) Int. Cl.
*A61B 17/32* (2006.01)

(52) U.S. Cl.
CPC ............. *A61B 17/320068* (2013.01); *A61B 2017/320072* (2013.01); *A61B 2017/320075* (2017.08);
(Continued)

(58) Field of Classification Search
CPC .............. A61B 17/1644; A61B 17/142; A61B 17/320068; A61B 2017/1651;
(Continued)

(56) References Cited

U.S. PATENT DOCUMENTS 5,122,142 A 6/1992 Pascaloff
5,261,922 A * 11/1993 Hood ............. A61B 17/320068
606/167

(Continued)

FOREIGN PATENT DOCUMENTS

CN 101677826 A 3/2010
CN 102046297 A 5/2011
(Continued)

OTHER PUBLICATIONS

International Search Report and Written Opinion dated Nov. 13, 2017 for International Application No. PCT/US2017/033536, 19 pages.

(Continued)

*Primary Examiner* — Erich G Herbermann
(74) *Attorney, Agent, or Firm* — Frost Brown Todd LLC

(57) ABSTRACT

A bone cutting surgical instrument includes features to mitigate heat generation during use. Excessive heat can be detrimental to bone health as well as to the instrument itself. In one example a liquid dispensing feature provides a flow of cooling liquid to an ultrasonic blade via a lumen in a waveguide of the instrument. In another example, the blade has a serrated edge with a plurality of teeth arranged in a pattern to provide dimension and space during cutting actions. In another example, the blade has an oversize distal portion that creates an oversize slot when cutting to avoid excessive contact between the cut bone and proximal portions of the blade. In another example the blade includes an irrigation slot and also a micro slot in a distal end of the blade that connects with the irrigation slot.

17 Claims, 18 Drawing Sheets

(52) U.S. Cl.
CPC ............. *A61B 2017/320084* (2013.01); *A61B 2217/007* (2013.01)

(58) Field of Classification Search
CPC ....... A61B 2017/320084; A61B 2017/320072; A61B 2217/007; A61B 2017/320069; A61B 2017/32007; A61B 2017/320074; A61B 2017/320075; A61B 2017/320077; A61B 2017/320052; A61B 2017/32009; A61B 17/3209; A61B 17/3211
See application file for complete search history.

(56) References Cited

U.S. PATENT DOCUMENTS

| | | | |
|---|---|---|---|
| 5,322,055 A | 6/1994 | Davison et al. | |
| 5,873,873 A | 2/1999 | Smith et al. | |
| 5,980,510 A | 11/1999 | Tsonton et al. | |
| 6,325,811 B1 | 12/2001 | Messerly | |
| 6,443,969 B1 | 9/2002 | Novak et al. | |
| 6,773,444 B2 | 8/2004 | Messerly | |
| 6,783,524 B2 | 8/2004 | Anderson et al. | |
| D680,218 S * | 4/2013 | Darian | D24/144 |
| 8,461,744 B2 | 6/2013 | Wiener et al. | |
| 8,591,459 B2 | 11/2013 | Clymer et al. | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 5/2015 | Miller et al. | |
| 9,241,730 B2 | 1/2016 | Babaev | |
| 9,381,058 B2 | 7/2016 | Houser et al. | |
| 10,660,663 B2 | 5/2020 | Madan et al. | |
| 10,702,296 B2 | 7/2020 | Boudreaux et al. | |
| 2004/0030254 A1 | 2/2004 | Babaev | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0188878 A1* | 8/2008 | Young | A61B 17/144 606/169 |
| 2008/0200940 A1 | 8/2008 | Eichmann et al. | |
| 2011/0125174 A1 | 5/2011 | Babaev | |
| 2012/0116265 A1 | 5/2012 | Houser et al. | |
| 2012/0130380 A1* | 5/2012 | Babaev | A61B 17/142 606/82 |
| 2013/0072950 A1* | 3/2013 | Ross | A61B 17/3211 606/169 |
| 2013/0090576 A1 | 4/2013 | Stulen et al. | |
| 2015/0148832 A1 | 5/2015 | Boudreaux et al. | |
| 2016/0106455 A1 | 4/2016 | Aldridge et al. | |

FOREIGN PATENT DOCUMENTS

| | | |
|---|---|---|
| CN | 204133550 U | 2/2015 |
| WO | WO 1994/015538 A1 | 7/1994 |

OTHER PUBLICATIONS

U.S. Appl. No. 61/410,129, filed Nov. 5, 2010.
U.S. Appl. No. 61/410,603, filed Nov. 5, 2010.
Brazilian Examination Report dated Jan. 7, 2022 for Application No. BR 112018074157-4, 5 pgs.
Chinese Search Report dated Nov. 25, 2020 for Application No. CN 2017800325043. 2pgs.
Chinese Office Action, The Second Office Action, and Supplementary search, dated Jul. 19, 2021 for Application No. CN 201780032504.3.
European Examination Report dated Oct. 13, 2021 For Application No. EP 17728321.5. 5 pgs.
Indian Examination Report dated Jun. 23, 2021 for Application No. IN 20181743251. 7 pgs.
Japanese Office Action, Notice of Reasons for Refusal, dated Apr. 6, 2021 for Application No. JP 2018-561536, 6 pgs.
Japanese Office Action, Notification of Reasons for Refusal, Final, dated Dec. 21, 2021, for Application No. JP 2018-561536,.
Korena Office Action, Notice of Submission of Opinion, dated Mar. 16, 2022 for Application No. KR 10-2018-7037458, 12 pgs.

* cited by examiner

ULTRASONIC SURGICAL INSTRUMENT BLADE WITH HEAT REDUCTION FEATURE

This application is a continuation of U.S. patent application Ser. No. 15/163,830, entitled "Ultrasonic Surgical Instrument Blade with Heat Reduction Feature," filed May 25, 2016 and issued as U.S. Pat. No. 10,660,663 on May 26, 2020.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Ultrasonic surgical instruments such as those described in the above-cited references may be primarily used to sever and/or seal soft tissue. However, it may be desirable to use an ultrasonic surgical instrument to cut bone, in addition to or as an alternative to cutting/sealing soft tissue. Cutting bone with an ultrasonic surgical instrument may generate more heat than cutting/sealing soft tissue with an ultrasonic surgical instrument. Unless properly addressed, this additional heat may cause undesirable effects, such as damage (e.g., necrosis) to adjacent bone and/or tissue; and/or damage to the ultrasonic blade.

Some conventional ultrasonic surgical instruments may be configured to use fluid to cool an ultrasonic blade. Examples of such instruments are described in U.S. Pub. No. 2015/0148832, entitled "Features to Apply Fluid to an Ultrasonic Blade of a Surgical Instrument," published May 28, 2015, issued as U.S. Pat. No. 10,034,685 on Jul. 31, 2018 the disclosure of which is incorporated by reference herein. Other examples of ultrasonic surgical instruments that are configured to communicate fluid are described in U.S. Pub. No. 2013/0090576, entitled "Surgical Instrument with Ultrasonic Waveguide Defining a Fluid Lumen," published Apr. 11, 2013, now abandoned, the disclosure of which is incorporated by reference herein; and U.S. Pat. No. 8,591,459, entitled "Use of Biomarkers and Therapeutic Agents with Surgical Devices," issued Nov. 26, 2013, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
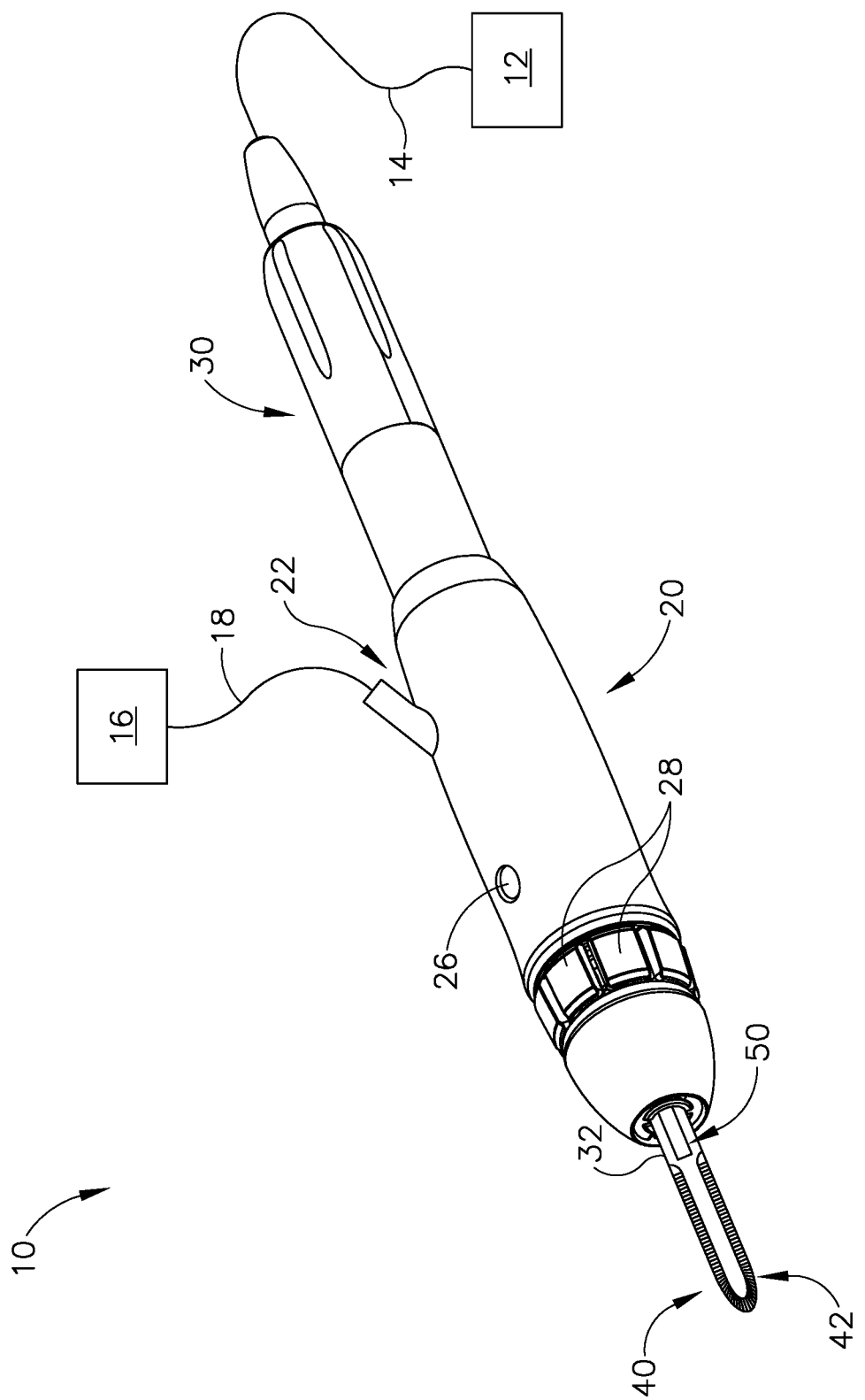
FIG. 1 depicts a perspective view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument with Serrated Blade and Liquid Cooling Feature FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), an ultrasonic transducer assembly (30), an ultrasonic blade (40), and a liquid dispensing feature (50). Handle assembly (20) is configured to be grasped using a pencil grip, though some operators may choose to grasp handle assembly (20) in some other fashion (e.g., using a power grip, etc.). Handle assembly (20) includes a fluid port (22), a fluid switch (26), and a plurality of activation buttons (28).

Fluid port (22) is configured to couple with a fluid conduit (18), which is further in communication with a fluid source (16). Fluid conduit (18) may comprise a flexible tube and/or any other kind of conduit (18). By way of example only, fluid conduit (18) may be coupled with fluid port (22) via a luer fitting and/or any other suitable kind(s) of connection features. Fluid source (16) may comprise a soft container (e.g., a bag), a hard container (e.g., a box or canister), or have any other suitable configuration. In some versions, fluid source (16) is not pressurized, such that fluid flows from fluid source (16) to port under the influence of gravity. In some other versions, fluid source (16) is pressurized. For instance, fluid source (16) may comprise a pump or other pressurizing assembly. As another merely illustrative example, fluid source (16) may contain a pre-pressurized fluid.

In any of the foregoing versions, fluid switch (26) is operable to selectively control the flow of fluid from fluid source (16) to liquid dispensing feature (50). For instance, fluid switch (26) may be operable to actuate a valve to transition the valve between an open state and a closed state. In some other versions, fluid switch (26) is omitted and the flow of fluid from fluid source (16) to liquid dispensing feature (50) is either constant or is regulated automatically. Various components and configurations that may be used to selectively restrict the flow of fluid from fluid source (16) to liquid dispensing feature (50) will be apparent to those of ordinary skill in the art in view of the teachings herein. It should also be understood that any suitable fluids may be communicated from fluid source (16) to liquid dispensing feature (50) to cool a surgical site, including but not limited to saline.

Ultrasonic transducer assembly (30) extends proximally from handle assembly (20) and is coupled with a generator (12) via a cable (14), such that transducer assembly (30) receives electrical power from generator (12). Piezoelectric elements in transducer assembly (30) convert that electrical power into ultrasonic vibrations. Generator (12) may include a power source and control module that is configured to provide a power profile to transducer assembly (30) that is particularly suited for the generation of ultrasonic vibrations through transducer assembly (30). By way of example only, generator (12) may comprise a GEN04 or GEN11 sold by Ethicon Endo-Surgery, Inc. of Cincinnati, Ohio. In addition, or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. In versions where generator (12) is capable of driving various different kinds of ultrasonic surgical instruments (e.g., with different resonant frequencies), handle assembly (20) may include an EEPROM or some other feature that identifies the type of ultrasonic surgical instrument (10) for generator (12), such that generator (12) may automatically select and deliver the appropriate power profile based on the identified type of ultrasonic surgical instrument (10).

It should also be understood that at least some of the functionality of generator (12) may be integrated into handle assembly (20), and that handle assembly (20) may even include a battery or other on-board power source such that cable (14) is omitted. Still other suitable forms that generator (12) may take, as well as various features and operabilities that generator (12) may provide, will be apparent to those of ordinary skill in the art in view of the teachings herein.

In the present example, transducer assembly (30) is activated in response to the operator actuating at least one button (28) of handle assembly (20). Buttons (28) are provided in an angularly spaced array about the longitudinal axis defined by handle assembly (20). The configuration and arrangement of buttons (28) in the present example enables an operator to easily access and actuate at least one button (28) regardless of the angular orientation of handle assembly (20) in the operator's hand. In other words, the operator will be able to easily actuate at least one button (28) with the thumb or index finger of the operator's hand that is grasping handle assembly (20) using a pencil grip. By way of example only, buttons (28) may be configured and operable in accordance with at least some of the teachings of U.S. patent application Ser. No. 14/515,129, entitled "Activation Features for Ultrasonic Surgical Instrument," filed Oct. 15, 2014, issued as U.S. Pat. No. 9,907,565 on Mar. 6, 2018, the disclosure of which is incorporated by reference herein. Alternatively, handle assembly (20) may have any other suitable user input features that are operable to selectively activate transducer assembly (30). As yet another merely illustrative alternative, transducer assembly (30) may be selectively activated using some other kind of user input (e.g., footswitch, etc.).

Ultrasonic blade (40) of the present example includes a serrated edge (42) extending around the outer perimeter of blade (40). Ultrasonic blade (40) is acoustically coupled with ultrasonic transducer assembly (30) via a waveguide (32), which extends through handle assembly (20) to join transducer assembly (30) with blade (40). Thus, ultrasonic vibrations that are generated by transducer assembly (30) are communicated along waveguide (32) to blade (40), such that blade (40) will vibrate ultrasonically when transducer assembly (30) is activated. Those of ordinary skill in the art will understand that, as a matter of physics, the distal end of blade (40) is located at a position corresponding to an anti-node associated with resonant ultrasonic vibrations communicated through waveguide (32) (i.e., at an acoustic anti-node).

When transducer assembly (30) is energized, the distal end of blade (40) is configured to move longitudinally in the range of, for example, approximately 10 to 500 microns peak-to-peak, and in some instances in the range of about 20 to about 200 microns at a predetermined vibratory frequency $f_0$ of, for example, approximately 21 kHz to approximately 31 kHz. In some other versions, the vibratory frequency is up to approximately 50 kHz or even up to approximately 55 kHz. At any such frequencies, when blade (40) is pressed against bone as described in greater detail below, the ultrasonic oscillation of blade (40) will work in concert with sharp edge (42) to break up the bone to promote cutting of the bone by blade (40).

Liquid dispensing feature (50) of the present example is in the form of a tube having an open distal end that is located near the position where blade (40) extends from waveguide (32). It should be understood that no portions of liquid dispensing feature (50) contact blade (40) in this example. Moreover, liquid dispensing feature (50) has sufficient rigidity in this example such that liquid dispensing feature (50) will not contact blade (40) even if liquid dispensing feature (50) is pressed against bone or other structures during normal operation of instrument (10).

The tube forming liquid dispensing feature (50) is parallel to waveguide (32) and blade (40) and is laterally offset from waveguide (32) and blade (40). Liquid dispensing feature (50) is in fluid communication with conduit (18) via port (22), such that liquid dispensing feature (50) is operable to expel cooling liquid from fluid source (16) via the open distal end of liquid dispensing feature (50). Due to the positioning of liquid dispensing feature (50) in relation to blade (40), the expelled cooling liquid will flow along blade (40) and along the bone that is being engaged by blade (40), thereby providing a cooling effect to blade (40) and the adjacent bone. As noted above, when an ultrasonic blade is used to cut through bone, the friction caused by the blade vibrating against the bone may generate substantial heat, which may be undesirable. Thus, liquid dispensing feature (50) may be used to dispense cooling liquid at a bone cut site in order to avoid undesirable effects from excess heat generated by blade (40).

In the present example, the distal end of liquid dispensing feature (50) is located at a position corresponding to a node associated with ultrasonic vibrations communicated along waveguide (32) and blade (40). This may reduce the occurrence of waveguide (32) or blade (40) undesirably dispersing cooling liquid laterally away from blade (40) as soon as the cooling liquid exits the distal end of liquid dispensing feature (50).

While liquid dispensing feature (50) is disclosed herein as having the form of a tube with an open distal end, it should be understood that liquid dispensing feature (50) may take a variety of other forms. By way of example only, liquid dispensing feature (50) may be configured and operable in accordance with any of the various liquid dispensing features described in U.S. patent application Ser. No. 15/163,811, entitled "Ultrasonic Surgical Instrument with Cooling Conduit," filed on May 25, 2016, published as U.S. Pub. No. 2017/0340344 on Nov. 30, 2017, issued as U.S. Pat. No. 10,702,296 on Jul. 7, 2020, the disclosure of which is incorporated by reference herein. Other suitable forms that liquid dispensing feature (50) may take will be apparent to those of ordinary skill in the art in view of the teachings herein. In some alternative versions, liquid dispensing feature (50) is omitted entirely. It should therefore be understood that the following examples may be provided without liquid cooling, if desired.

Figure 2:
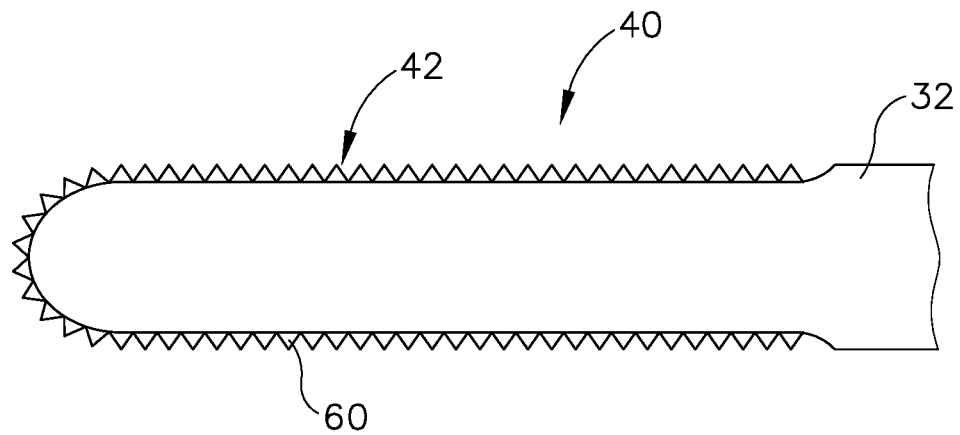
FIG. 2 depicts a top plan view of an ultrasonic blade of the instrument of FIG. 1.
Figure 3:
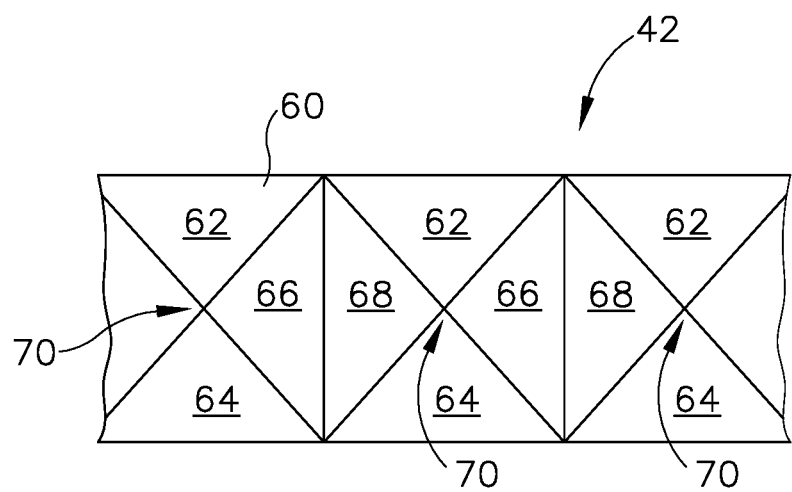
FIG. 3 depicts a partial side elevational view of the ultrasonic blade of FIG. 2.

As noted above, blade (40) of the present example has a serrated edge (42). As best seen in FIGS. 2-3, serrated edge (42) comprises a plurality of teeth (60). As best seen in FIG. 3, each tooth (60) comprises a pyramid shape with triangular surfaces (62, 64, 66, 68) extending outward from blade (40) and converging to form a peak (70). A valley is defined where surface (66) of one tooth (60) meets surface (68) of an adjacent tooth (60). Spacing between adjacent peaks (70) or valleys may also be referred to as the tooth spacing or spacing between adjacent teeth (60). In the present example, the spacing between adjacent teeth (60) is maintained to be less than the size of the wavelength of the ultrasonic vibrations communicated through blade (40). For example, in the present example the spacing between adjacent peaks (70) or valleys is in the range of about $\frac{1}{1000}^{th}$ to about $\frac{1}{10}^{th}$ of the harmonic wavelength. By way of example only, and not limitation, in a system with a vibratory frequency of 55 kHz, this spacing would be in the range of about 0.004 inches to about 0.04 inches. Other tooth spacing configurations relative to the harmonic wavelength will be apparent to those of ordinary skill in the art in view of the teachings herein.

Serrated edge (42) can be manufactured in a variety of ways that will be apparent to those of ordinary skill in the art in view of the teachings herein. For example, some manufacturing applications may include photo etching, printing a coating on blade (40), laser machining, and cold forming, among others.

The pyramid shape of teeth (60) provide a three dimensional surface. This three dimensional surface provides air space between adjacent teeth (60). When performing an ultrasonic cut on bone, or tissue for that matter, fluid can fill the air space between adjacent teeth (60). In one example, the fluid can be a cooling liquid meant to cool the bone or tissue being cut. In another example, the fluid can be a cooling gas or air meant to cool the bone or tissue being cut. In the illustrated version, one air space between adjacent teeth (60) is defined by adjacent surface (66) and surface (68) that also define a valley between peaks (70). Other air spaces are defined by surface (62) and surface (64) that converge at respective peaks (70). These surfaces (62, 64) define a partial or half valley orthogonally positioned to the valley defined by adjacent surfaces (66, 68). While the present example illustrates teeth (60) as having a three dimensional shape that comprises a pyramid shape, in view of the teachings herein, other three dimensional shapes or patterns for teeth (60) will be apparent to those of ordinary skill in the art.

Figure 4:
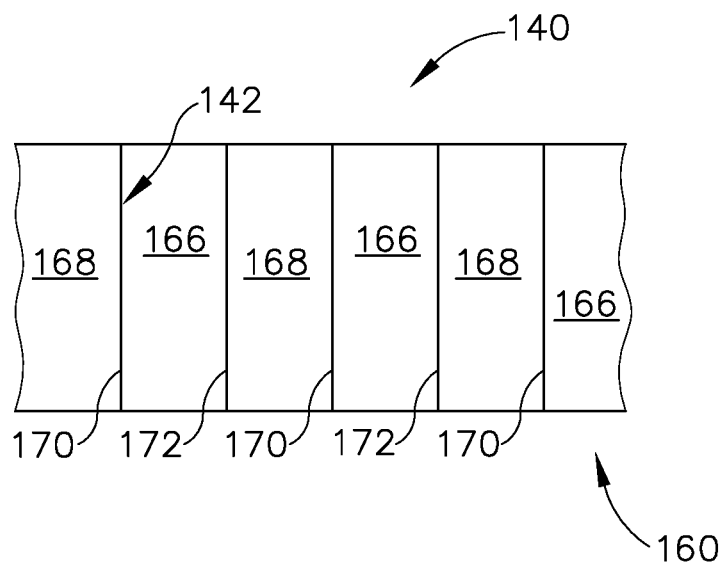
FIG. 4 depicts a partial side elevational view of an exemplary alternative ultrasonic blade that may be incorporated into the instrument of FIG. 1.
Figure 5:
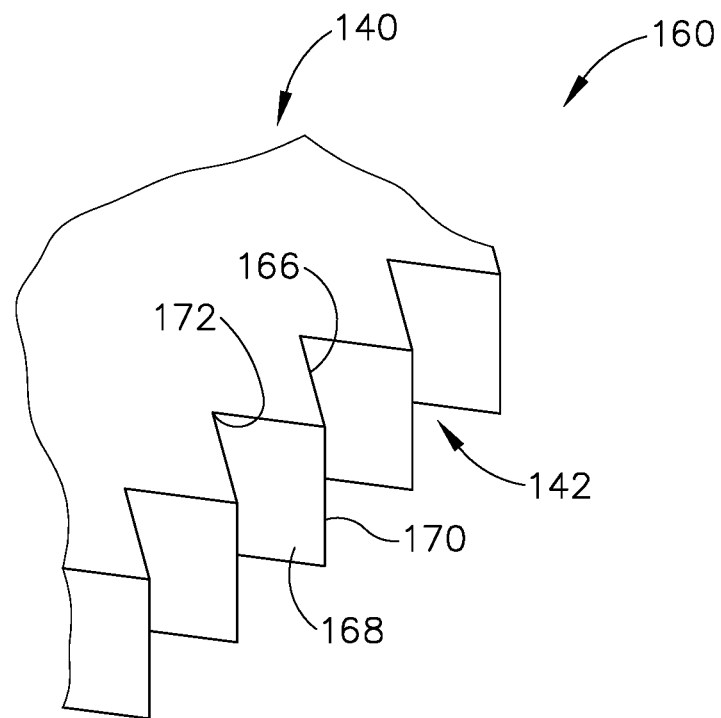
FIG. 5 depicts a partial perspective view of the ultrasonic blade of FIG. 4.
Figure 6:
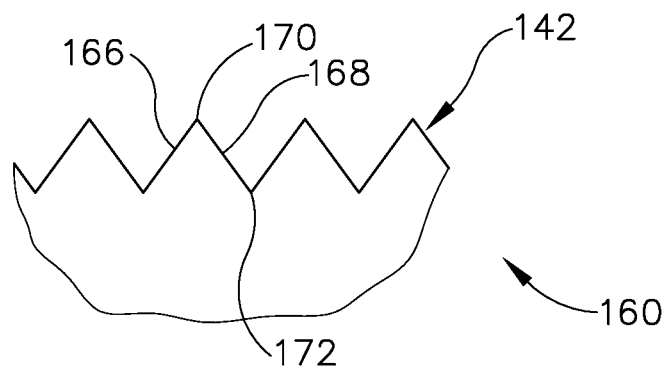
FIG. 6 depicts a partial top plan view of the ultrasonic blade of FIG. 4.

FIGS. 4-6 show another exemplary serrated ultrasonic blade (140) that may be incorporated into instrument (10) in place of blade (40). Blade (140) of this example also has a serrated edge (142), but in this example a plurality of teeth (160) is formed from repeating triangular shaped teeth (160). Each tooth (160) comprises a first sloped surface (166), a second sloped surface (168), and a peak (170). Peak (170) is defined at the intersection of first sloped surface (166) and second sloped surface (168) for each respective tooth (160). Valleys (172) are defined between adjacent teeth (160). In this manner, the intersection of first sloped surface (166) of one tooth (160) with second sloped surface (168) of an adjacent tooth (160) defines valley (172). While not required in all versions, in the present example, teeth (160) repeat in a uniform fashion such that each tooth (160) is generally the same size.

Spacing between adjacent peaks (170) or valleys (172) may be referred to as the tooth spacing or spacing between adjacent teeth (160). In the present example, the spacing between adjacent teeth (160) is maintained to be less than the size of the wavelength of the ultrasonic vibrations communicated through blade (140). For example, in the present example the spacing between adjacent peaks (170) or valleys (172) is in the range of about $\frac{1}{1000}^{th}$ to about $\frac{1}{10}^{th}$ of the harmonic wavelength. By way of example only, and not limitation, in a system with a vibratory frequency of 55 kHz, this spacing would be in the range of about 0.004 inches to about 0.04 inches. Other tooth spacing configurations relative to the harmonic wavelength will be apparent to those of ordinary skill in the art in view of the teachings herein.

Serrated edge (142) can be manufactured in a variety of ways that will be apparent to those of ordinary skill in the art in view of the teachings herein. For example, some manufacturing applications may include photo etching, printing a coating on blade (140), laser machining, and cold forming, among others.

The triangular shape of teeth (160) provide a three dimensional surface. This three dimensional surface provides air space between adjacent teeth (160). When performing an ultrasonic cut on bone, or tissue for that matter, fluid can fill the air space between adjacent teeth (160). In one example, the fluid can be a cooling liquid meant to cool the bone or tissue being cut. In another example, the fluid can be a cooling gas or air meant to cool the bone or tissue being cut. In the illustrated version, one air space between adjacent teeth (160) is defined by adjacent surface (166) and surface (168) that also define valley (172) between peaks (170). This air space repeats along serrated edge (142) of blade (140). While the present example illustrates teeth (160) as having a three dimensional shape that comprises a triangular shape, in view of the teachings herein, other three dimensional shapes or patterns for teeth (160) will be apparent to those of ordinary skill in the art.

Figure 7:
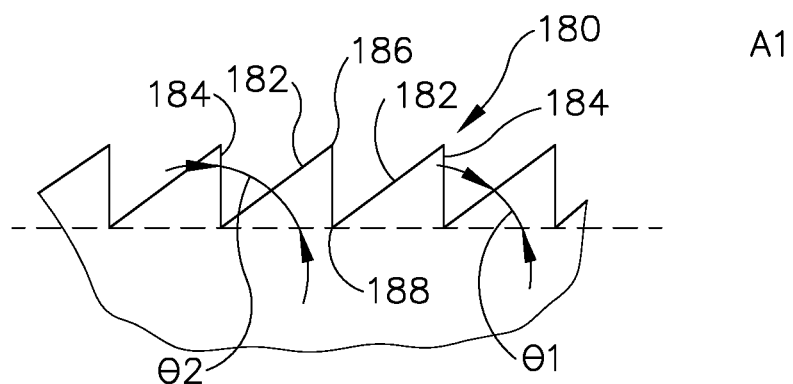
FIG. 7 depicts a partial top plan view of another exemplary ultrasonic blade that may be incorporated into the instrument of FIG. 1.

FIG. 7 shows another exemplary serrated ultrasonic blade (180) that may be incorporated into instrument (10) in place of blade (40). Blade (180) of this example is similar to blade (140) and can be manufactured in the same or similar ways as blade (140). Blade (180) comprises alternating first sloped surfaces (182) and second sloped surfaces (184). Peaks (186) are defined at the intersection of first sloped surface (182) and second sloped surface (184) for each respective tooth. Valleys (188) are defined between adjacent teeth, or at the intersection of first sloped surface (182) of one tooth and second sloped surface (184) of an adjacent tooth. Spacing between adjacent peaks (186) or valleys (188) may be referred to as the tooth spacing or spacing between adjacent teeth. In the present example, the spacing between adjacent teeth is maintained to be less than the size of the wavelength of the ultrasonic vibrations communicated through blade (180). For example, in the present example the spacing between adjacent peaks (186) or valleys (188) is in the range of about $1/1000^{th}$ to about $1/10^{th}$ of the harmonic wavelength. By way of example only, and not limitation, in a system with a vibratory frequency of 55 kHz, this spacing would be in the range of about 0.004 inches to about 0.04 inches. Other tooth spacing configurations relative to the harmonic wavelength will be apparent to those of ordinary skill in the art in view of the teachings herein.

In the present example, blade (180) defines a longitudinal axis (A1) along its length. First sloped surfaces (182) define a first angle (θ1) with longitudinal axis (A1), and second sloped surfaces (184) define a second angle (θ2) with longitudinal axis (A1). First angle (θ1) is an acute angle and is less than second angle (θ2). Second angle (θ2) is an obtuse angle. However, in another example second angle (θ2) is about a ninety-degree angle. In yet another example, second angle (θ2) is an acute angle greater than first angle (θ1). With the configuration of first and second sloped surfaces (182, 184), relative to longitudinal axis (A1), the slope of surface (182) is less or not as steep as the slope of surface (184). Unlike blades (40, 140), with the angles and slopes as described, each of the plurality of teeth are not symmetrical about an orthogonal axis to longitudinal axis (A1) where the orthogonal axis extends through peaks (186).

Blade (180) comprises triangular shaped teeth that provide a three dimensional surface. This three dimensional surface provides air space between adjacent teeth. When performing an ultrasonic cut on bone, or tissue for that matter, fluid can fill the air space between adjacent teeth. In one example, the fluid can be a cooling liquid meant to cool the bone or tissue being cut. In another example, the fluid can be a cooling gas or air meant to cool the bone or tissue being cut. In the illustrated version, one air space between adjacent teeth is defined by adjacent surface (182) and surface (184) that also define valley (188) between peaks (186). This air space repeats along the serrated edge of blade (180). While the present example illustrates teeth as having a three dimensional shape that comprises a triangular shape, in view of the teachings herein, other three dimensional shapes or patterns for teeth will be apparent to those of ordinary skill in the art.

Figure 8:
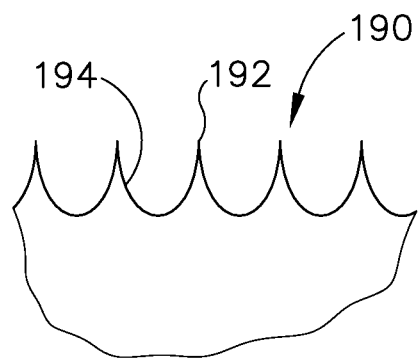
FIG. 8 depicts a partial top plan view of another exemplary ultrasonic blade that may be incorporated into the instrument of FIG. 1.

FIG. 8 shows another exemplary serrated ultrasonic blade (190) that may be incorporated into instrument (10) in place of blade (40). Blade (190) of this example is similar to blade (140) and can be manufactured in the same or similar ways as blade (140). Blade (190) comprises a repeating scalloped surface (194) that extends from a peak (192) of one tooth on blade (190) to another peak (192) of an adjacent tooth on blade (190). In this manner, peaks (192) are defined at the intersection of repeating scalloped surfaces (194), with valleys defined between peaks (194). Spacing between adjacent peaks (192) or valleys may be referred to as the tooth spacing or spacing between adjacent teeth. In the present example, the spacing between adjacent teeth is maintained to be less than the size of the wavelength of the ultrasonic vibrations communicated through blade (190). For example, in the present example the spacing between adjacent peaks (192) or valleys is in the range of about $1/1000^{th}$ to about $1/10^{th}$ of the harmonic wavelength. By way of example only, and not limitation, in a system with a vibratory frequency of 55 kHz, this spacing would be in the range of about 0.004 inches to about 0.04 inches. Other tooth spacing configurations relative to the harmonic wavelength will be apparent to those of ordinary skill in the art in view of the teachings herein.

Blade (190) comprises pointed shaped teeth that provide a three dimensional surface. This three dimensional surface provides air space between adjacent teeth. When performing an ultrasonic cut on bone, or tissue for that matter, fluid can fill the air space between adjacent teeth. In one example, the fluid can be a cooling liquid meant to cool the bone or tissue being cut. In another example, the fluid can be a cooling gas or air meant to cool the bone or tissue being cut. In the illustrated version, one air space between adjacent teeth is defined by scalloped surface (194) that also defines valleys between peaks (192). This air space repeats along the serrated edge of blade (190). While the present example illustrates teeth as having a three dimensional shape that comprises a pointed shape, in view of the teachings herein, other three dimensional shapes or patterns for teeth will be apparent to those of ordinary skill in the art.

Figure 9:
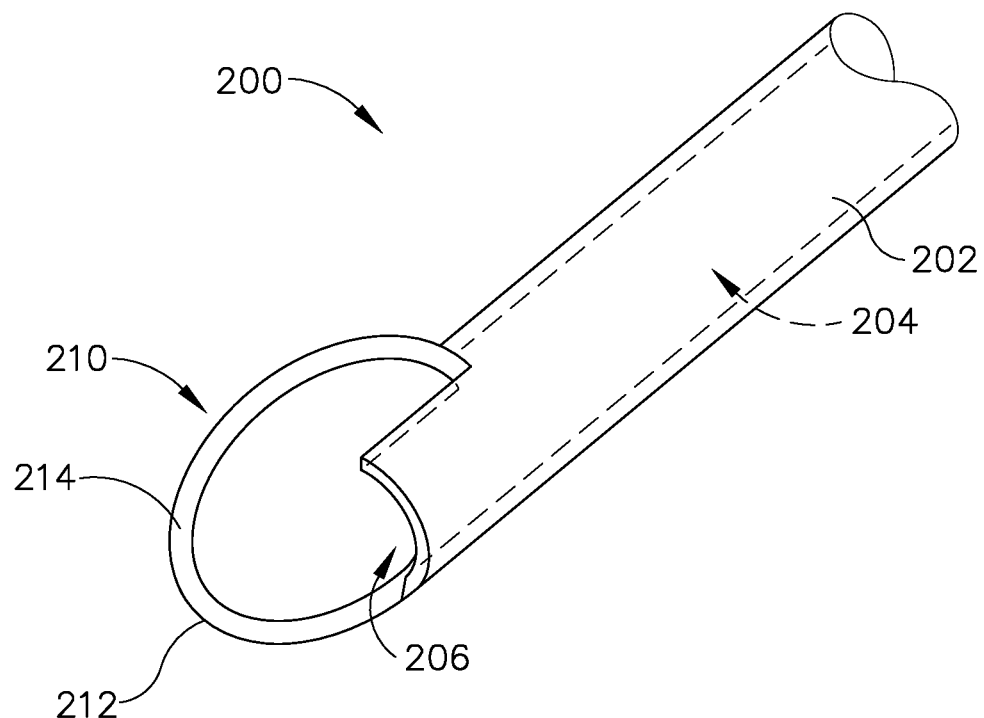
FIG. 9 depicts a perspective view of another exemplary ultrasonic blade and a distal portion of an acoustic waveguide that may be incorporated into the instrument of FIG. 1.
Figure 10:
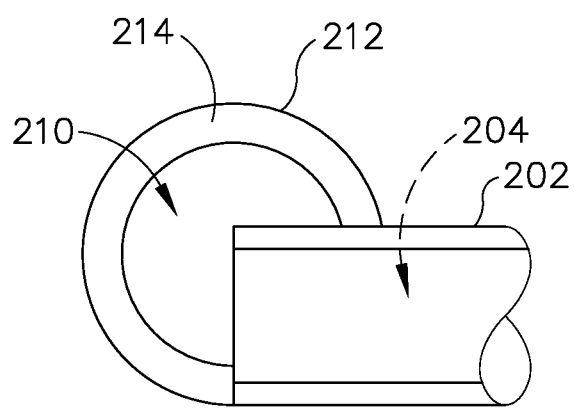
FIG. 10 depicts a side elevational view of the ultrasonic blade and acoustic waveguide of FIG. 9.
Figure 11:
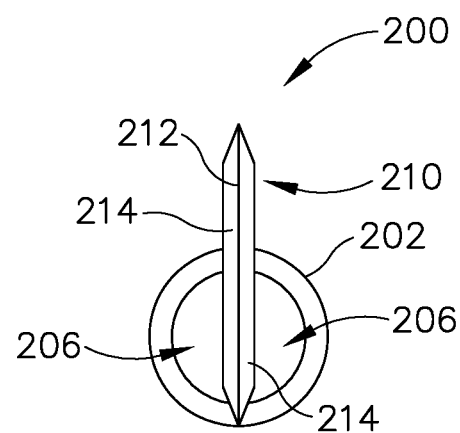
FIG. 11 depicts an end view of the ultrasonic blade and acoustic waveguide of FIG. 9.

II. Exemplary Ultrasonic Surgical Instrument with Lobe Blade and Coolant Lumen in Waveguide In some instances, it may be desirable to minimize contact between bone and the proximal portion of an ultrasonic blade, such that only the distal portion of the ultrasonic blade contacts the bone. This is due to the fact that only the distal portion of the ultrasonic blade is actually cutting the bone, while the proximal portion of the ultrasonic blade may be simply generating unnecessary (and possibly destructive) heat. To that end, FIGS. 9-11 show an exemplary alternative end effector (200) that minimizes unnecessary contact between non-cutting proximal portions of the acoustic drivetrain; while maintaining contact between productively cutting distal portions of the acoustic drivetrain. In particular, end effector (200) of this example comprises an ultrasonic blade (210) and waveguide (202) that may be incorporated into instrument (10) in place of blade (40) and waveguide (32), with liquid dispensing feature (50) being omitted.

While blade (210) and waveguide (202) are being described in the context of instrument (10), it should be understood that blade (210) and waveguide (202) may be incorporated into any other kind of ultrasonic surgical instrument. Waveguide (202) of the present example defines a lumen (204) and a pair of distal openings (206). Lumen (204) is in fluid communication with fluid source (16) via port (22) and conduit (18) in this example. It should therefore be understood that cooling liquid may be communicated to and through lumen (204), with the cooling liquid eventually being expelled via openings (206) as described in greater detail below.

Blade (210) of the present example comprises a generally lobe shape or disc shape. A pair of tapered surfaces (214) surround the perimeter of blade (210). Tapered surfaces (214) intersect to define a cutting edge (212) extending around the perimeter of blade (210). In some versions, but not required in all versions, tapered surfaces (214) comprise channels or holes configured to carry cooling fluid closer to the cutting site during use. In such versions where tapered surfaces (214) comprise channels or holes, cutting edge (212) remains uninterrupted by such channels or holes so that cutting edge (212) is continuous around the perimeter of blade (210).

Blade (210) connects with waveguide (202) in an inset configuration such that waveguide (202) extends past the proximal portion of blade (210) to about midway of the length of blade (210). With the shape of blade (210) and the configuration of waveguide (202), distal openings (206) of waveguide (202) are positioned closer to the portion of blade (210) where cutting occurs, compared to, e.g., the embodiment illustrated in FIG. 1. With this configuration, excessive misting and bubbling of the cooling fluid is minimized so as to not inhibit the user's field of view. Also this configuration provides delivery of, or the ability to deliver, cooling fluid closer to the cutting area where heat generation occurs, and with greater control and precision compared to some other configurations. For example, in use when a tip of blade (210) may be buried in bone in a bone cutting process, cooling fluid can be carried or delivered to this tip portion of blade (210).

In addition to expelling cooling fluid closer to the portion of blade (210) where cutting occurs, in a cutting application excessive heat generation can occur along the proximal regions of blades. In the present example, cooling fluid would emerge from distal openings (206) on each side of cutting edge (212) of blade (210) as seen best in FIG. 11. Furthermore, with the configuration of waveguide (202) as described above, the cooling fluid is directed out from distal openings (206) to the proximal regions of blade (210) to prevent or combat excessive heat generation during cutting. In the illustrated version of FIGS. 9-11, blade (210) extends upward from waveguide (202) such a longitudinal centerline of waveguide (202) aligns with a lower quarter of blade (210) with an upper portion of waveguide (202) aligned with about the center of blade (210). With this configuration, the released cooling fluid initially contacts half the surface of blade (210) on both sides of blade (210), and then flows to the remaining surface of blade (210).

Figure 12:
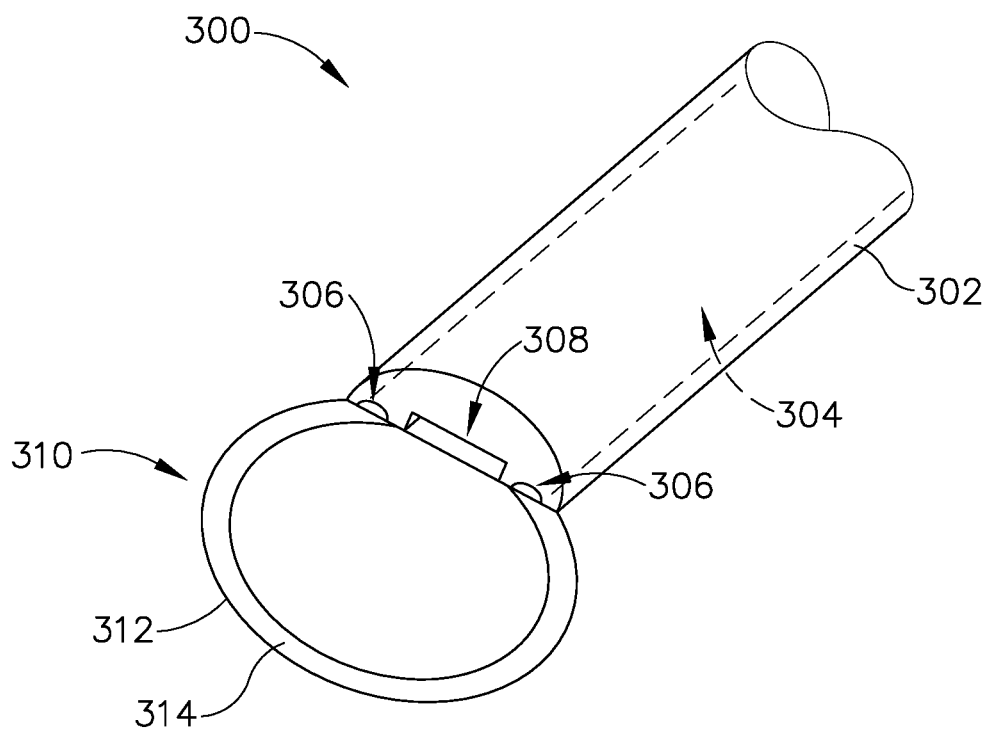
FIG. 12 depicts a perspective view of another exemplary ultrasonic blade and a distal portion of an acoustic waveguide that may be incorporated into the instrument of FIG. 1.
Figure 13:
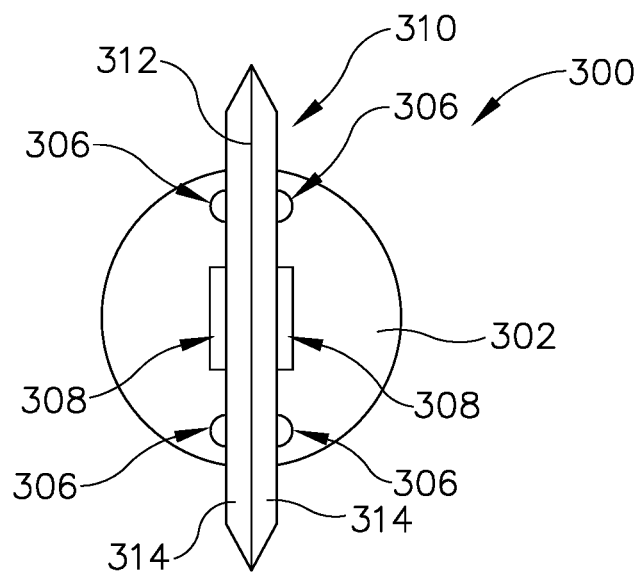
FIG. 13 depicts an end view of the ultrasonic blade and acoustic waveguide of FIG. 12.

FIGS. 12-13 depict another exemplary end effector (300) comprising an ultrasonic blade (310) and waveguide (302) that may be incorporated into instrument (10) in place of blade (40) and waveguide (32), with liquid dispensing feature (50) being omitted. While blade (310) and waveguide (302) are being described in the context of instrument (10), it should be understood that blade (310) and waveguide (302) may be incorporated into any other kind of ultrasonic surgical instrument. Waveguide (302) of the present example defines a lumen (304) and a set of distal openings (306, 308). Lumen (304) is in fluid communication with fluid source (16) via port (22) and conduit (18) in this example. It should therefore be understood that cooling liquid may be communicated to and through lumen (304), with the cooling liquid eventually being expelled via openings (306, 308) as described in greater detail below.

Blade (310) of the present example comprises a generally lobe shape or disc shape. A pair of tapered surfaces (314) surround the perimeter of blade (310). Tapered surfaces (314) intersect to define a cutting edge (312) extending around the perimeter of blade (310). In some versions, but not required in all versions, tapered surfaces (314) comprise channels or holes configured to carry cooling fluid closer to the cutting site during use. In such versions where tapered surfaces (314) comprise channels or holes, cutting edge (312) remains uninterrupted by such channels or holes so that cutting edge (312) is continuous around the perimeter of blade (310).

Blade (310) connects with waveguide (302) such that waveguide (302) abuts the proximal portion of blade (310). With the shape of blade (310) and the configuration of waveguide (302), distal openings (306, 308) of waveguide (302) are positioned closer to the portion of blade (310) where cutting occurs, compared to, e.g., the embodiment illustrated in FIG. 1. With this configuration, excessive misting and bubbling of the cooling fluid is minimized so as to not inhibit the user's field of view. Also this configuration provides delivery of, or the ability to deliver, cooling fluid closer to the cutting area where heat generation occurs, and with greater control and precision compared to some other configurations. For example, in use when a tip of blade (310) may be buried in bone in a bone cutting process, cooling fluid can be carried or delivered to this tip portion of blade (310).

In addition to expelling cooling fluid closer to the portion of blade (310) where cutting occurs, in a cutting application excessive heat generation can occur along the proximal regions of blades. In the present example, cooling fluid would emerge from distal openings (306, 308) on each side of cutting edge (312) of blade (310) as seen best in FIG. 13. Furthermore, with the configuration of waveguide (302) as described above, the cooling fluid is directed out from distal openings (306, 308) to the proximal regions of blade (310) to prevent or combat excessive heat generation during cutting. In the illustrated version of FIGS. 12-13, blade (310) is centered with waveguide (302) such a longitudinal centerline of waveguide (302) aligns with about the center of blade (310). With this configuration, the released cooling fluid initially contacts the surface of blade (310) near its center on both sides of blade (310), and then flows to the more distal surfaces of blade (310).

In the present example, distal openings (308) are similar to distal openings (206) described above with respect to blade (210). However, distal openings (308) in the present example have a rectangular shape as opposed to the half circle shape of distal openings (206) with blade (210). In view of the teachings herein, various modifications to the shape of distal openings (308) and or distal openings (206) will be apparent to those of ordinary skill in the art. Distal openings (306) in the illustrated example of FIGS. 12-13 align with tapered surface (314) of blade (310) as best seen in FIG. 12. As discussed above, in some versions tapered surface (314) includes holes or channels to carry cooling fluid around the perimeter of blade (310) to provide cooling fluid to cutting edge (312) around the perimeter of blade (310). In versions without such holes or channels in tapered surface (314) cooling fluid is still able to flow along tapered surface (314) to provide cooling fluid to cutting edge (312) around the perimeter of blade (310).

In the present example, there are multiple sets of distal openings (306, 308). More specifically, one set of distal openings (308) provides for greater cooling fluid volume to be delivered to the surfaces of blade (310) compared to the other set of distal openings (306). In this manner, distal openings (308) provide larger openings compared to the openings for distal openings (306). In view of the teachings herein, other modifications to sets of distal openings (306, 308) will be apparent to those of ordinary skill in the art. For example, the size of the relative size of the openings may be larger or smaller, and/or the number of sets of distal openings may also be greater or fewer in other modified versions.

Figure 14:
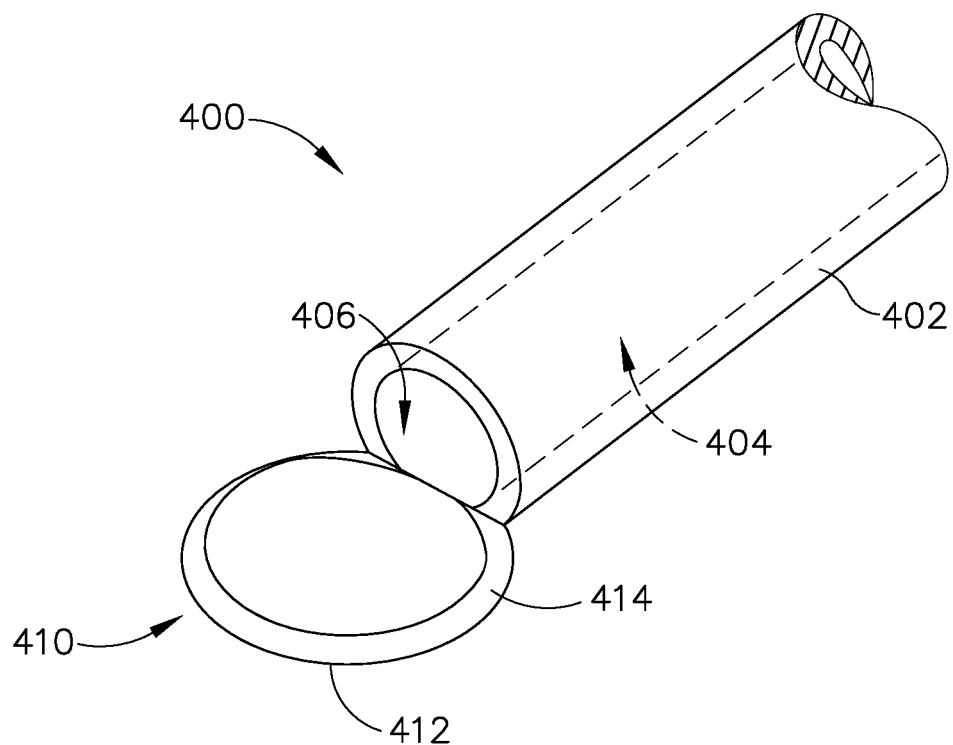
FIG. 14 depicts a perspective view of another exemplary ultrasonic blade and a distal portion of an acoustic waveguide that may be incorporated into the instrument of FIG. 1.
Figure 15:
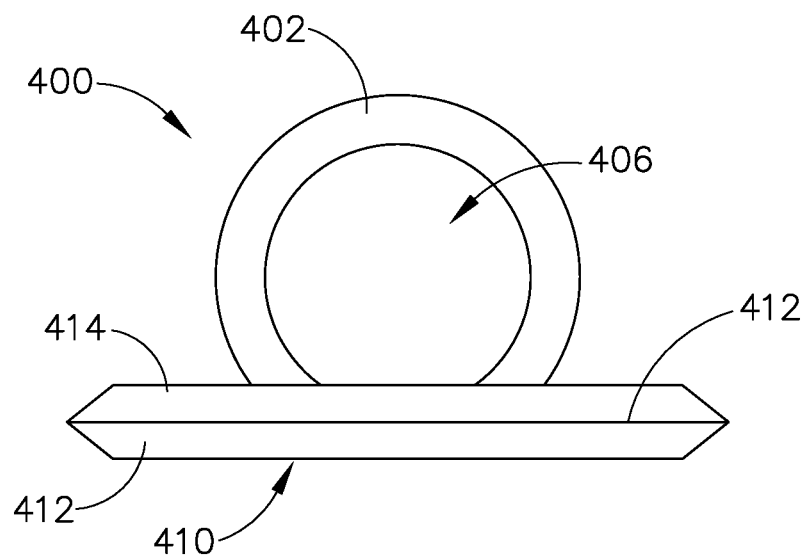
FIG. 15 depicts an end view of the ultrasonic blade and acoustic waveguide of FIG. 14.

FIGS. 14-15 depict another exemplary end effector (400) comprising an ultrasonic blade (410) and waveguide (402) that may be incorporated into instrument (10) in place of blade (40) and waveguide (32), with liquid dispensing feature (50) being omitted. While blade (410) and waveguide (402) are being described in the context of instrument (10), it should be understood that blade (410) and waveguide (402) may be incorporated into any other kind of ultrasonic surgical instrument. Waveguide (402) of the present example defines a lumen (404) and a distal opening (406). Lumen (404) is in fluid communication with fluid source (16) via port (22) and conduit (18) in this example. It should therefore be understood that cooling liquid may be communicated to and through lumen (404), with the cooling liquid eventually being expelled via opening (406) as described in greater detail below.

Blade (410) of the present example comprises a generally lobe shape or disc shape. A pair of tapered surfaces (414) surround the perimeter of blade (410). Tapered surfaces (414) intersect to define a cutting edge (412) extending around the perimeter of blade (410). In some versions, but not required in all versions, tapered surfaces (414) comprise channels or holes configured to carry cooling fluid closer to the cutting site during use. In such versions where tapered surfaces (414) comprise channels or holes, cutting edge (412) remains uninterrupted by such channels or holes so that cutting edge (412) is continuous around the perimeter of blade (410).

Blade (410) connects with waveguide (402) such that waveguide (402) abuts the proximal portion of blade (410). With the shape of blade (410) and the configuration of waveguide (402), distal opening (406) of waveguide (402) is positioned closer to the portion of blade (410) where cutting occurs, compared to, e.g., the embodiment illustrated in FIG. 1. With this configuration, excessive misting and bubbling of the cooling fluid is minimized so as to not inhibit the user's field of view. Also this configuration provides delivery of, or the ability to deliver, cooling fluid closer to the cutting area where heat generation occurs, and with greater control and precision compared to some other configurations. For example, in use when a tip of blade (410) may be buried in bone in a bone cutting process, cooling fluid can be carried or delivered to this tip portion of blade (410).

In addition to expelling cooling fluid closer to the portion of blade (410) where cutting occurs, in a cutting application excessive heat generation can occur along the proximal regions of blades. In the present example, cooling fluid would emerge from distal opening (406) on one side of cutting edge (412) of blade (410) as seen best in FIG. 15. Furthermore, with the configuration of waveguide (402) as described above, the cooling fluid is directed out from distal opening (406) to the proximal regions of blade (410) to prevent or combat excessive heat generation during cutting. In the illustrated version of FIGS. 14-15, a longitudinal centerline of waveguide (402) aligns with about the center of blade (410). With this configuration, the released cooling fluid initially contacts the surface of blade (410) on one side of blade (410), and is then distributed to the cutting site to cool the bone and/or tissue being cut. In some examples when using end effector (400) having only a single distal opening (406) located on only one side of blade (410), enhanced visibility can be achieved at the cutting site.

While the present example, illustrates a single distal opening (406) positioned on one side of blade (410), in view of the teachings herein, other modifications to distal opening (406) will be apparent to those of ordinary skill in the art. For example, the size of distal opening (406) may be larger or smaller, and/or the number of distal openings may also be greater or fewer in other modified versions, e.g. having two or more distal openings located on one side of blade (410). Still in other versions, end effector (400) may be modified to be similar to end effector (200) where blade (410) is positioned to bisect distal opening (406) such that there may be multiple distal openings providing access to lumen (404).

Figure 16:
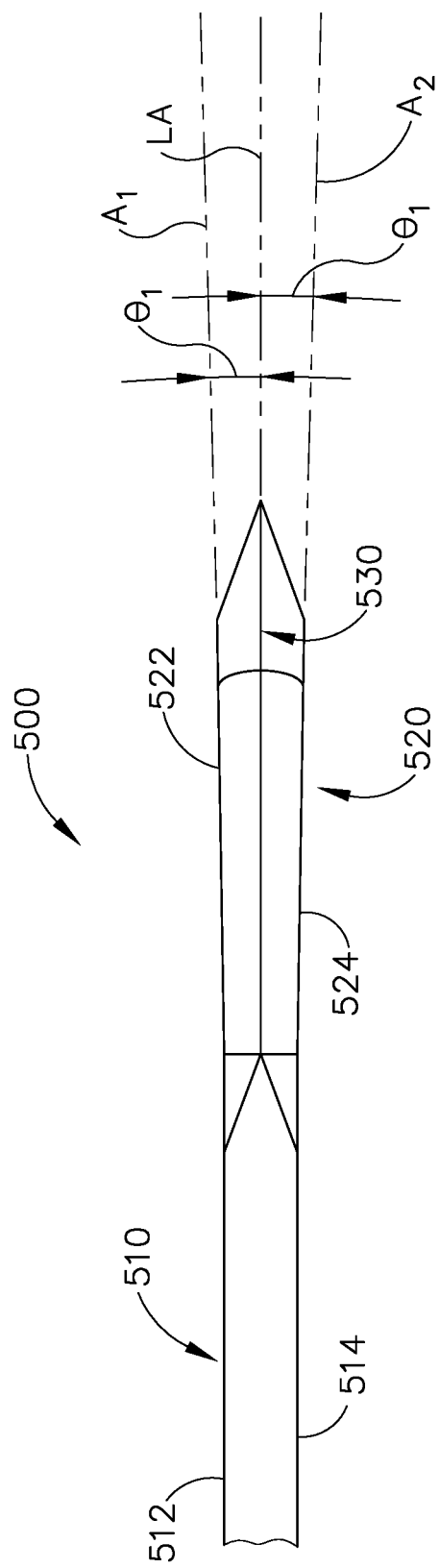
FIG. 16 depicts a side elevational view of another exemplary ultrasonic blade that may be incorporated into the instrument of FIG. 1.
Figure 17:
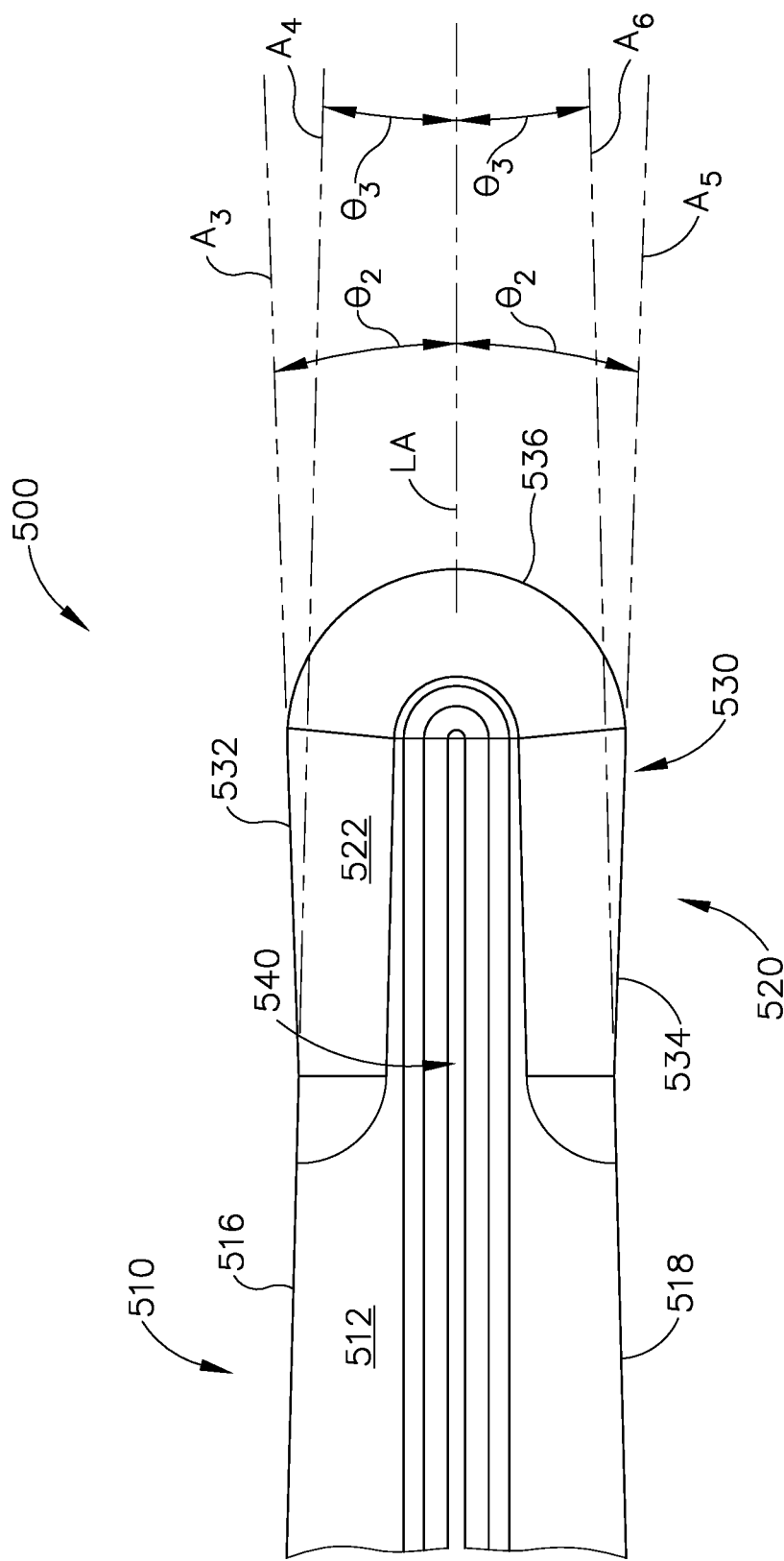
FIG. 17 depicts a top plan view of the ultrasonic blade of FIG. 16.

III. Exemplary Ultrasonic Surgical Instrument with Blade Having Oversize Distal End In some instances, an ultrasonic blade having a substantially flat profile may tend to get stuck in a kerf formed in bone. In addition or in the alternative, it may be difficult for cooling liquid to enter a kerf formed in bone when an ultrasonic blade having a substantially flat profile is disposed in the kerf. It may therefore be desirable to provide an ultrasonic blade with a distal portion that is wider and/or thicker than a proximal portion of the ultrasonic blade. Such a configuration may reduce the risk of the blade getting stuck in a kerf formed in bone. In addition or in the alternative, such a configuration may promote the ingress of cooling liquid into the kerf, even while the blade is disposed in the kerf. To that end, FIGS. 16-17 depict another exemplary ultrasonic blade (500) that may be incorporated into instrument (10) in place of blade (40). Alternatively, blade (500) may be incorporated into any other kind of ultrasonic surgical instrument, including instruments with or without liquid dispensing features like liquid dispensing feature (50). It should therefore be understood that blade (500) does not need to necessarily be used in conjunction with liquid cooling features, though blade (500) may be used with one or more liquid cooling features if desired.

Blade (500) of this example comprises a proximal end (510), an oversize distal end (520), a cutting edge (530), and an opening (540). Proximal end (510) comprises first surface (512), second surface (514), first edge (516), and second edge (518). Oversize distal end (520) comprises first surface (522) and second surface (524). Cutting edge (530) extends along the circumference of oversize distal end (520) and includes first cutting edge portion (532), second cutting edge portion (534), and third cutting edge portion (536).

In the present example, when cutting bone blade (500), with its oversize distal end (520), creates an oversize slot in outer bone, e.g. the cortical bone. Once blade (500) penetrates further into the bone, e.g. reaching the inner cancellous bone, the proximal end (510) of blade resides in the oversize slot formed by the cutting action achieved with oversize distal end (520). In this manner, because the proximal end (510) is smaller than the oversize slot created by oversize distal end (520) the chance or risk of blade (500) becoming stuck or lodged within the bone is reduced. Also, with the larger oversize slot created by oversize distal end (520) compared to the smaller proximal end (510), space is provided between the cut bone and proximal end (510) such that in instances where cooling fluid is used, such cooling fluid has an increased flow path into the cut bone to reach the cut bone for cooling as well as to reach the distal end (520) of blade (500) for cooling.

Referring to FIG. 16, blade (500) defines a longitudinal axis (LA). First surface (522) of distal end (520) defines a first axis (A1), and similarly second surface (524) of distal end (520) defines a second axis (A2). A first angle (θ1) is defined between first axis (A1) and longitudinal axis (LA), as well as between second axis (A2) and longitudinal axis (LA). In the present example, first angle (θ1) is an acute angle greater than zero degrees. By way of example only, and not limitation, in one example first angle (θ1) is about three degrees. In other examples first angle (θ1) can be greater or less than three degrees. Accordingly, first and second surfaces (522, 524) are not parallel with longitudinal axis (LA). As seen best in FIG. 16, with this configuration, the thickness of blade (500) increases in size as blade (500) extends distally up until the distal-most portion of blade (500) where there is a taper where blade (500) terminates in cutting edge (530). In this manner blade (500) comprises distal end (520) that is oversize in a first dimension that is perpendicular to longitudinal axis (LA). This first dimension may be referred to herein as coinciding with the thickness of blade (500).

Referring to FIG. 17, blade (500) defines longitudinal axis (LA) as described above. First cutting edge portion (532) of cutting edge (530) defines a third axis (A3), and similarly second cutting edge portion (534) of cutting edge (530) defines a fifth axis (A5). First edge (516) of proximal end (510) defines a fourth axis (A4), and similarly second edge (518) of proximal end (510) defines a sixth axis (A6). A second angle (θ2) is defined between third axis (A3) and longitudinal axis (LA), as well as between fifth axis (A5) and longitudinal axis (LA). A third angle (θ3) is defined between fourth axis (A4) and longitudinal axis (LA), as well as between sixth axis (A6) and longitudinal axis (LA).

In the present example, second angle (θ2) is an acute angle greater than zero degrees. By way of example only, and not limitation, in one example second angle (θ2) is about four degrees. In other examples second angle (θ2) can be greater or less than four degrees. Accordingly, first and second cutting edge portions (532, 534) are not parallel with longitudinal axis (LA). As seen best in FIG. 17, with this configuration, the width of distal end (520) of blade (500) increases in size as distal end (520) of blade (500) extends distally until the distal-most portion of blade (500) where blade (500) curves inward and terminates. In this manner blade (500) comprises distal end (520) that is oversize in a second dimension that is again perpendicular to longitudinal axis (LA). This second dimension may be referred to herein as coinciding with the width of blade (500).

In the present example, third angle (θ3) is an acute angle greater than zero degrees. By way of example only, and not limitation, in one example third angle (θ3) is about two degrees. In other examples third angle (θ3) can be greater or less than two degrees. Accordingly, first and second edges (516, 518) of proximal end (510) are not parallel with longitudinal axis (LA). As seen best in FIG. 17, with this configuration, the width of proximal end (510) of blade (500) is smallest where proximal end (510) meets distal end (520). When moving from the most-proximal region of proximal end (510) toward distal end (520), blade (500) decreases in width until reaching distal end (520) at which point blade (500) begins increasing in width as described above. In this manner the oversize configuration of distal end (520) of blade (500) is relative to the portion of proximal end (510) that is immediately adjacent distal end (520). As best seen in FIG. 17, the oversize configuration of distal end (520) of blade (500) is directed to the cutting region of blade (500), which coincides with distal end (520).

As mentioned above, blade (500) comprises opening (540). Opening (540) allows cooling fluid to flow between sides of blade (500). In this manner, heat generation that may be localized or more substantial on one side of blade (500) is able to be cooled even if the cooling fluid is first provided from the opposite side of blade (500).

Figure 18:
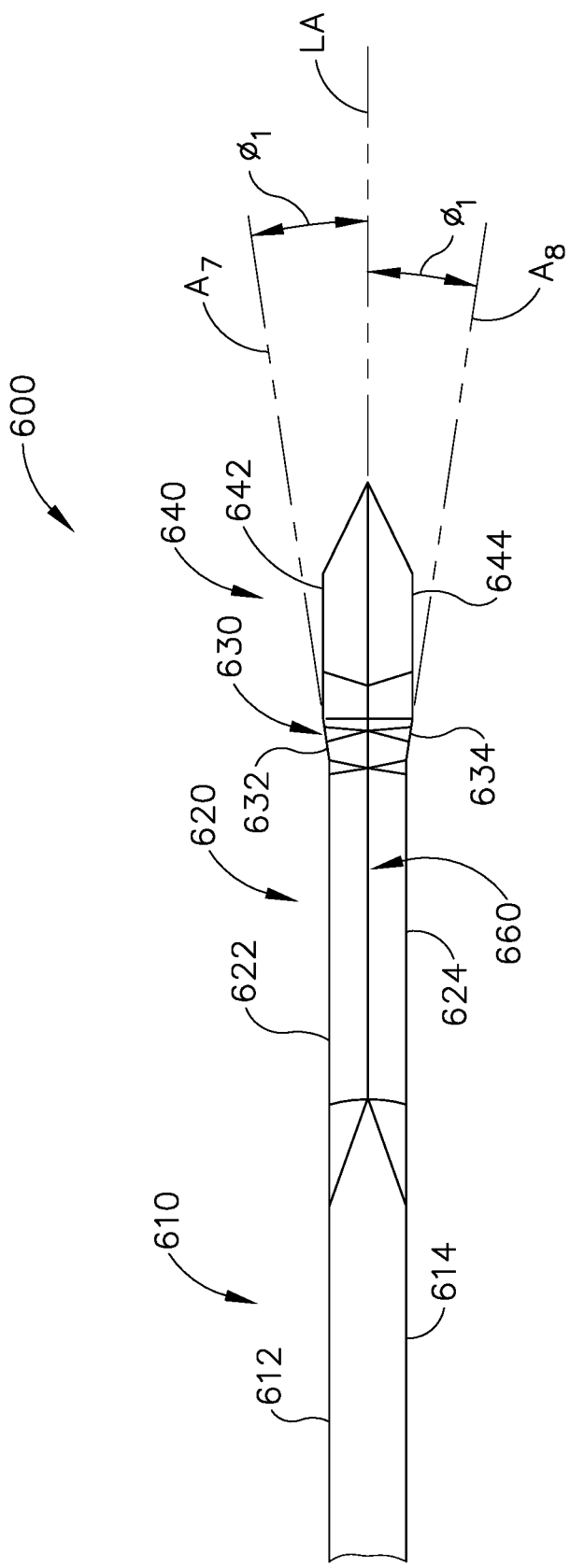
FIG. 18 depicts a side elevational view of another exemplary ultrasonic blade that may be incorporated into the instrument of FIG. 1.
Figure 19:
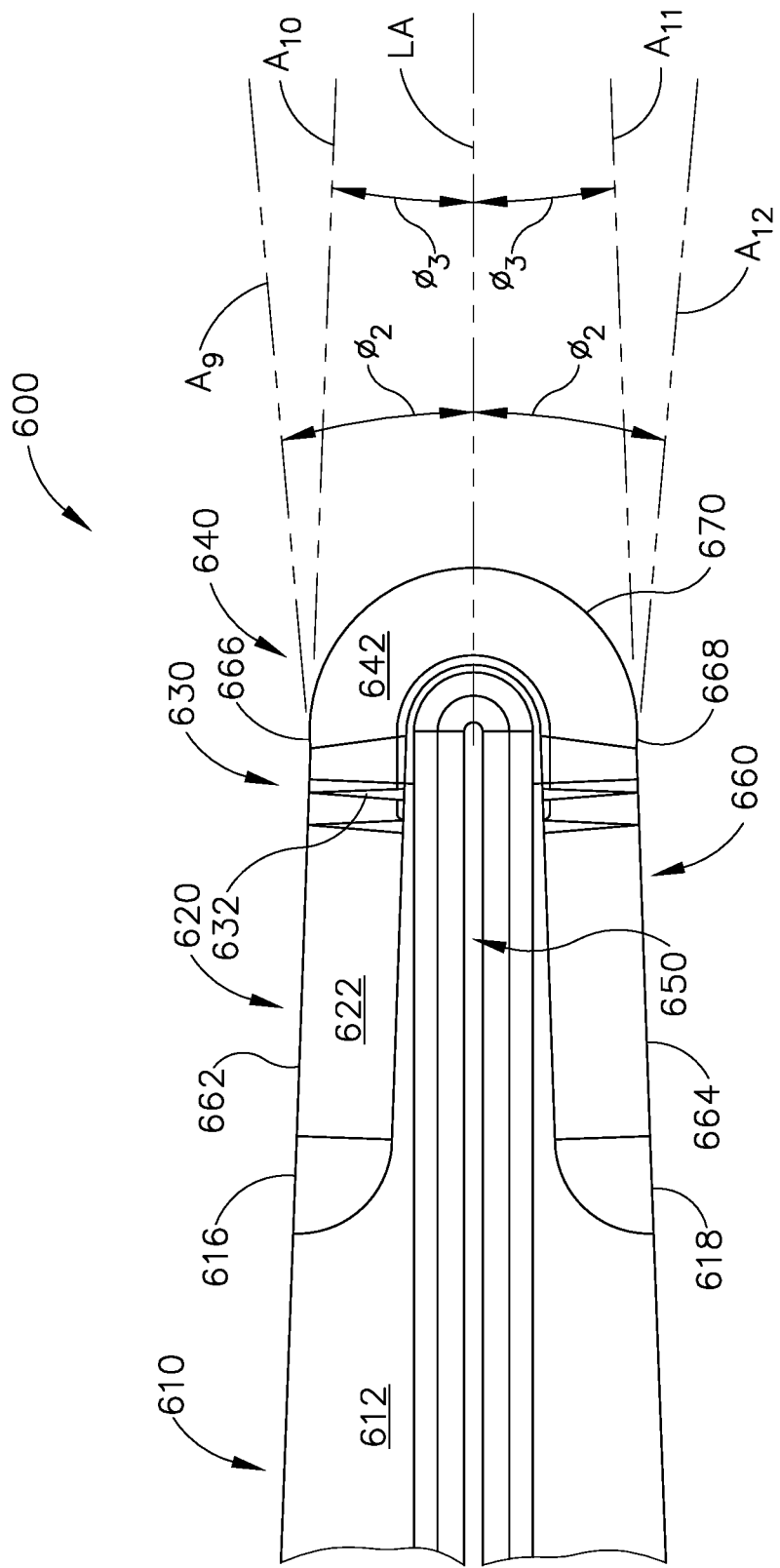
FIG. 19 depicts a top plan view of the ultrasonic blade of FIG. 18.

FIGS. 18-19 depict another exemplary ultrasonic blade (600) that may be incorporated into instrument (10) in place of blade (40). Alternatively, blade (600) may be incorporated into any other kind of ultrasonic surgical instrument, including instruments with or without liquid dispensing features like liquid dispensing feature (50). It should therefore be understood that blade (600) does not need to necessarily be used in conjunction with liquid cooling features, though blade (600) may be used with one or more liquid cooling features if desired.

Blade (600) of this example comprises a proximal end (610), a first distal region (620), a second distal region (640), a transition region (630) between first and second distal regions (620, 640), a cutting edge (660), and an opening (650). Proximal end (610) comprises first surface (612), second surface (614), first edge (616), and second edge (618). First distal region (620) comprises first surface (622) and second surface (624). Second distal region (640) comprises first surface (642) and second surface (644). Transition region (630) comprises first surface (632) and second surface (634). Cutting edge (660) extends along the circumference of first and second distal regions (620, 640) and includes first cutting edge portion (662), second cutting edge portion (666), third cutting edge portion (670), fourth cutting edge portion (668), and fifth cutting edge portion (664).

In the present example, second distal region (640) is oversize in a similar manner to oversize distal end (520) of blade (500). In the present example, when cutting bone blade (600), with its oversize second distal region (640), creates an oversize slot in outer bone, e.g. the cortical bone. Once blade (600) penetrates further into the bone, e.g. reaching the inner cancellous bone, the first distal region (620) of blade (600) resides in the oversize slot formed by the cutting action achieved with second distal region (640). In this manner, because first distal region (620) is smaller than the oversize slot created by oversize second distal region (640) the chance or risk of blade (600) becoming stuck or lodged within the bone is reduced. Also, with the larger oversize slot created by oversize second distal region (640) compared to the smaller first distal region (620), space is provided between the cut bone and first distal region (620) such that in instances where cooling fluid is used, such cooling fluid has an increased flow path into the cut bone to reach the cut bone for cooling as well as to reach second distal region (640) of blade (600) for cooling.

Referring to FIG. 18, blade (600) defines a longitudinal axis (LA) that aligns. First surface (632) of transition region (630) defines a seventh axis (A7), and similarly second surface (634) of transition region (630) defines an eighth axis (A8). A first angle (Ø1) is defined between seventh axis (A7) and longitudinal axis (LA), as well as between eighth axis (A8) and longitudinal axis (LA). In the present example, first angle (Ø1) is an acute angle greater than zero degrees. By way of example only, and not limitation, in one example first angle (Ø1) is about twenty degrees. In other examples first angle (Ø1) can be greater or less than twenty degrees. Accordingly, first and second surfaces (632, 634) are not parallel with longitudinal axis (LA). As seen best in FIG. 18, with this configuration, the thickness of blade (600) increases in size through transition region (630) as blade (600) extends distally up until transition region (630) ends and second distal region (640) begins at which point blade thickness remains constant as blade (600) extends distally until the distal-most portion of blade (600) where there is a taper where blade (600) terminates in cutting edge (660). In this manner blade (600) comprises an oversize second distal region (640) in a first dimension that is perpendicular to longitudinal axis (LA). This first dimension may be referred to herein as coinciding with the thickness of blade (600).

Referring to FIG. 19, blade (600) defines longitudinal axis (LA) as described above. A tangent line to second cutting edge portion (666) of cutting edge (660) defines a ninth axis (A9). First cutting edge portion (662) of cutting edge (660) defines a tenth axis (A10). Fifth cutting edge portion (664) of cutting edge (660) defines an eleventh axis (A11). A tangent line to fourth cutting edge portion (668) of cutting edge (660) defines a twelfth axis (A12). A second angle (Ø2) is defined between ninth axis (A9) and longitudinal axis (LA), as well as between twelfth axis (A12) and longitudinal axis (LA). A third angle (Ø3) is defined between tenth axis (A10) and longitudinal axis (LA), as well as between eleventh axis (A11) and longitudinal axis (LA).

In the present example, second angle (Ø2) is an acute angle greater than zero degrees. By way of example only, and not limitation, in one example second angle (Ø2) is about ten degrees. In other examples second angle (Ø2) can be greater or less than ten degrees. As seen best in FIG. 19, with this configuration, the width of blade (600) is widest between second and fourth cutting edge portions (666, 668). In this manner blade (600) comprises an oversize second distal region (640) in a second dimension that is again perpendicular to longitudinal axis (LA). This second dimension may be referred to herein as coinciding with the width of blade (600).

In the present example, third angle (Ø3) is an acute angle greater than zero degrees. By way of example only, and not limitation, in one example third angle (Ø3) is about three degrees. In other examples third angle (Ø3) can be greater or less than three degrees. Accordingly, first and fifth cutting edge portions (662, 664) of cutting edge (660) are not parallel with longitudinal axis (LA). As seen best in FIG. 19, with this configuration, the width of blade (600) at first distal region (620) is smallest where first distal region (620) meets transition region (630). When moving from the most-proximal region of first distal region (620) toward transition region (630), blade (600) decreases in width until reaching transition region (630) at which point blade (600) increases in width as described above. In this manner the oversize configuration of second distal region (640) of blade (600) is relative to the portion of first distal region (620) that is immediately adjacent transition region (630). As best seen in FIG. 19, the oversize configuration of second distal region (640) of blade (600) is directed to only that portion of the cutting region of blade (600) that coincides with transition region (630) and second distal region (640).

As mentioned above, blade (600) comprises opening (650). Opening (650) allows cooling fluid to flow between sides of blade (600). In this manner, heat generation that may be localized or more substantial on one side of blade (600) is able to be cooled even if the cooling fluid is first provided from the opposite side of blade (600).

Figure 20:
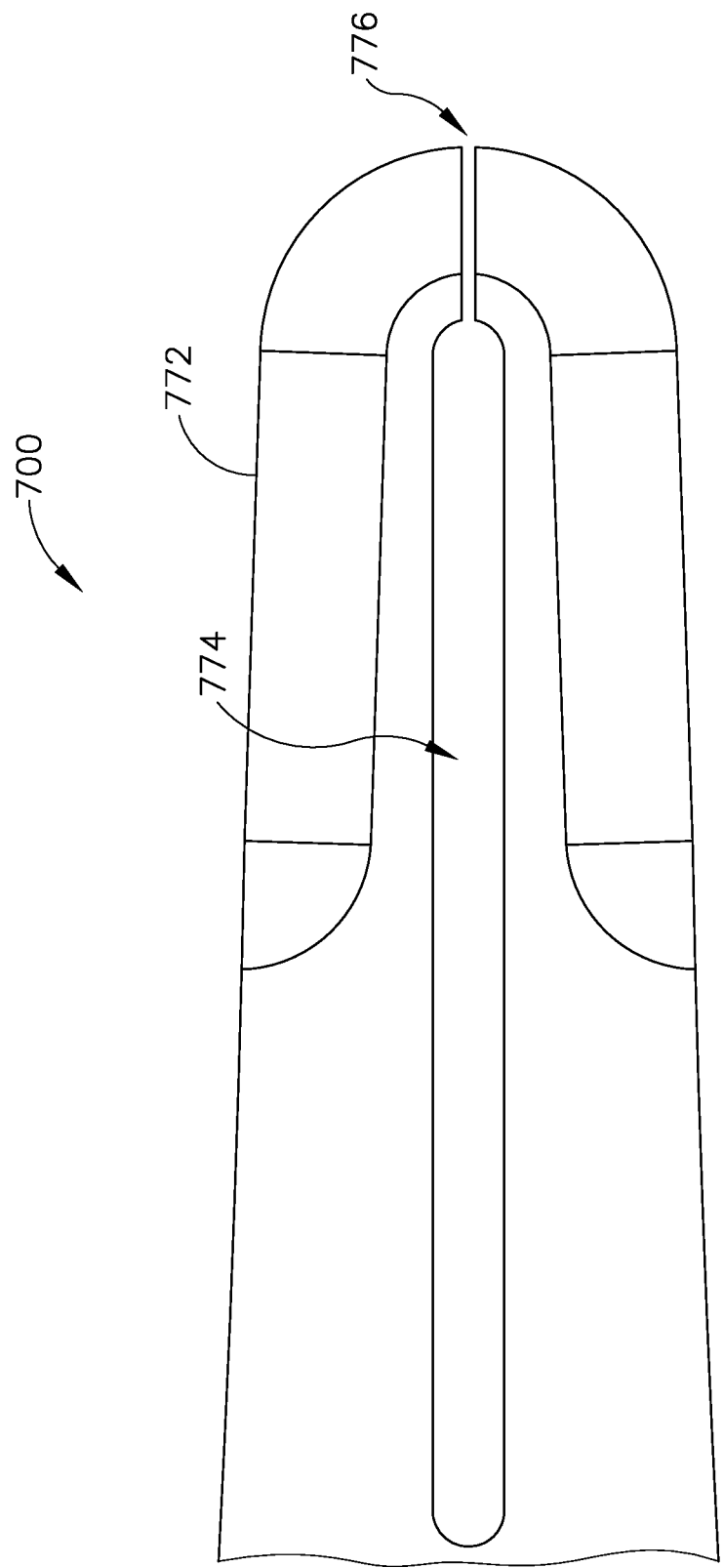
FIG. 20 depicts a top plan view of another exemplary ultrasonic blade that may be incorporated into the instrument of FIG. 1.
Figure 21:
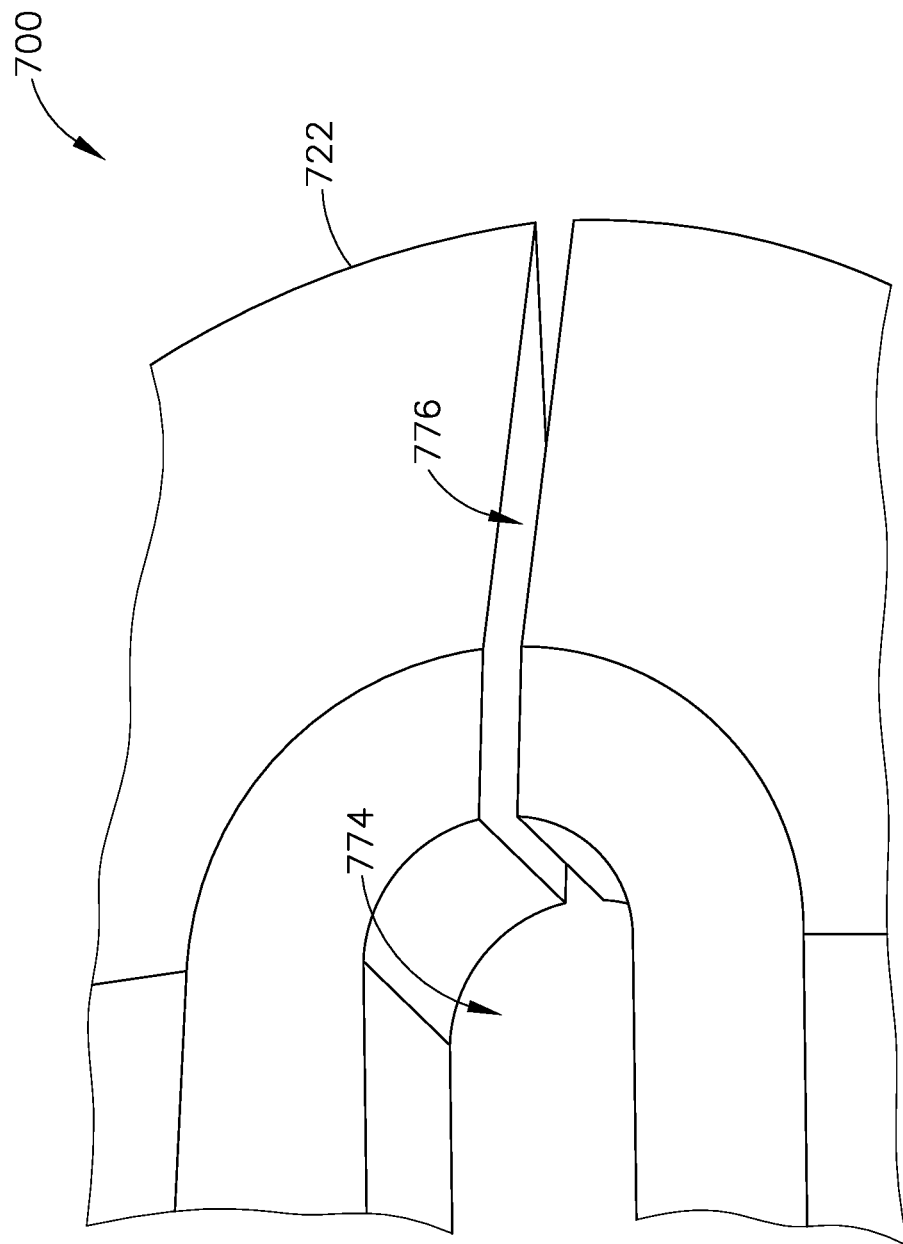
FIG. 21 depicts a partial perspective view of a distal end portion of the ultrasonic blade of FIG. 20.
Figure 22:
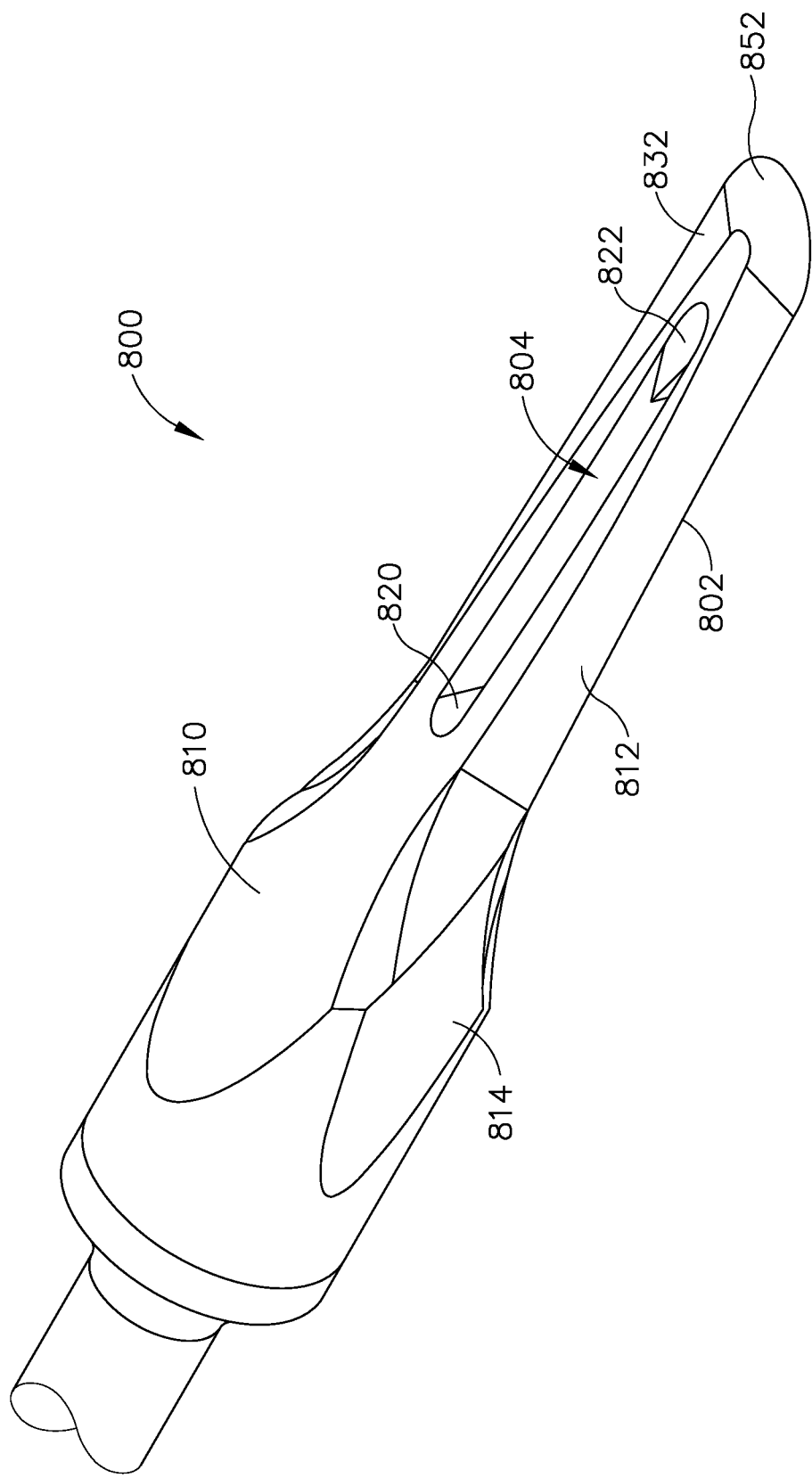
FIG. 22 depicts a perspective view of another exemplary ultrasonic blade that may be incorporated into the instrument of FIG. 1.
Figure 23:
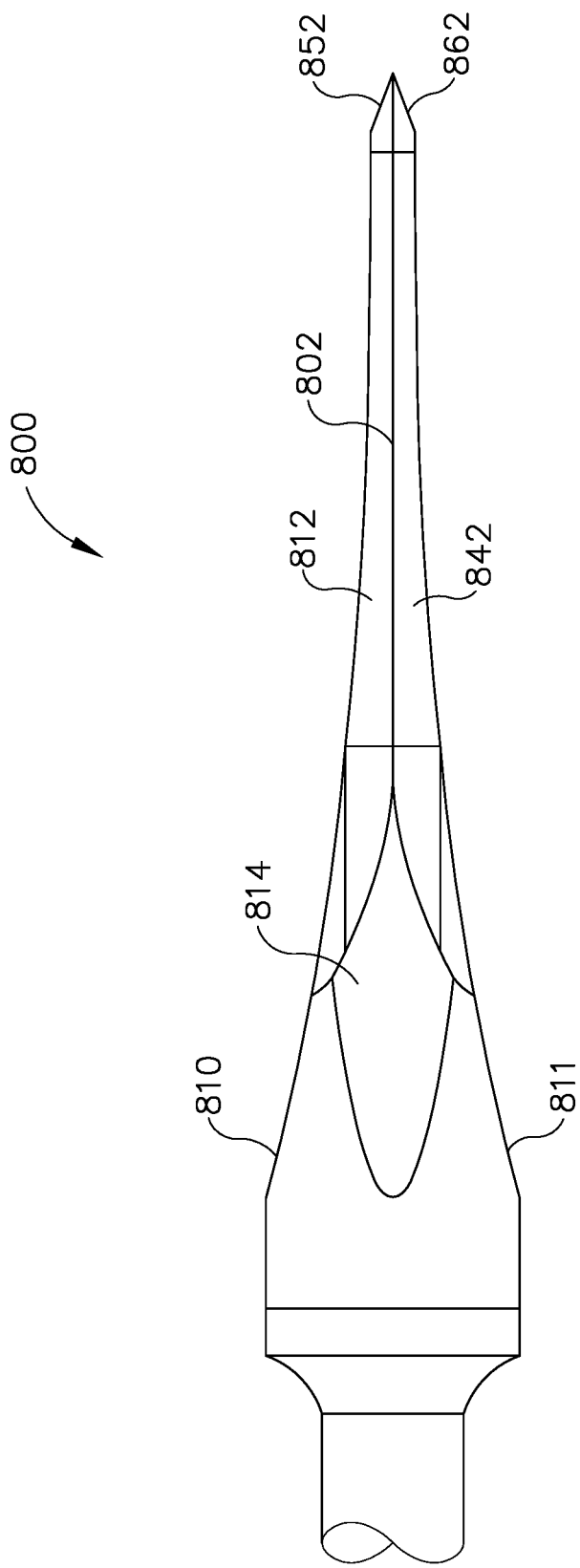
FIG. 23 depicts a side elevational view of the ultrasonic blade of FIG. 22.
Figure 24:
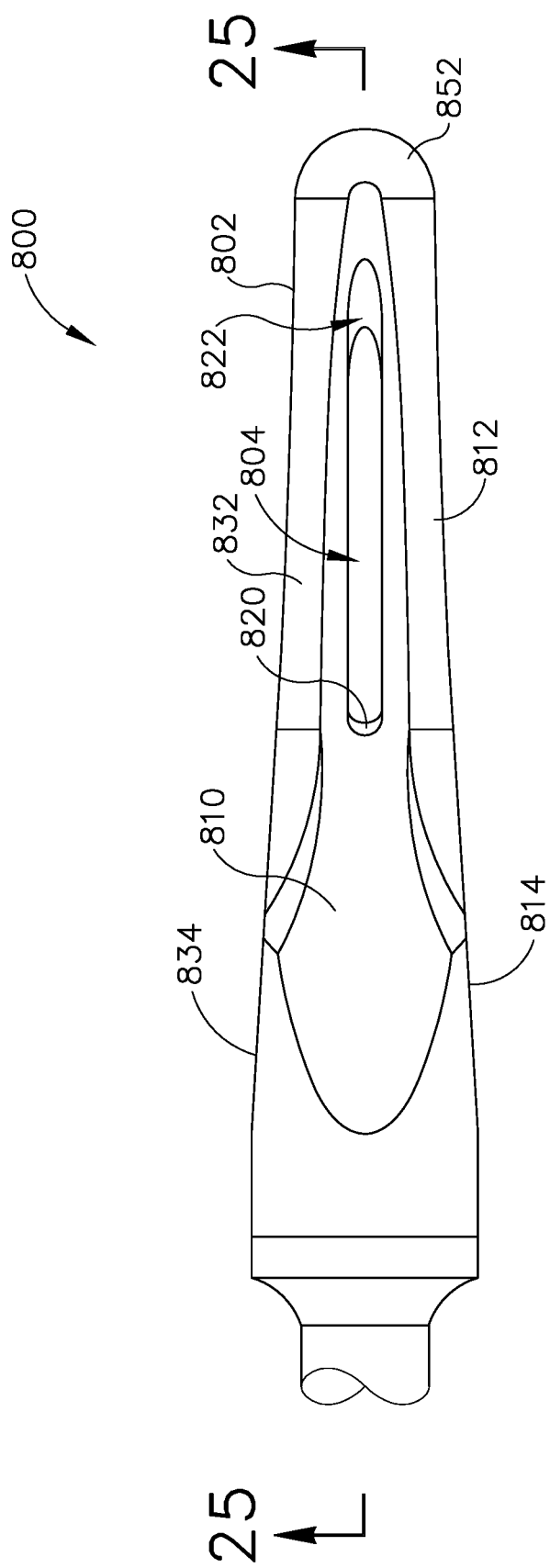
FIG. 24 depicts a top plan view of the ultrasonic blade of FIG. 22.

IV. Exemplary Ultrasonic Surgical Instrument with Blade Having Micro Slot at Distal End It may be desirable to configure an ultrasonic blade with features that promote travel of cooling liquid to the distal end of the blade. Such features may include recesses or openings that are sized and configured to convey or otherwise provide communication of cooling liquid. FIGS. 20-21 show an exemplary blade configuration that provides such fluid communication are described in greater detail below. In particular, FIGS. 20-21 depict another exemplary ultrasonic blade (700) that may be incorporated into instrument (10) in place of blade (40). Alternatively, blade (700) may be incorporated into any other kind of ultrasonic surgical instrument, including instruments with or without liquid dispensing features like liquid dispensing feature (50). It should therefore be understood that blade (700) does not need to necessarily be used in conjunction with liquid cooling features, though blade (700) may be used with one or more liquid cooling features if desired.

Blade (700) of this example comprises cutting edge (772) that extends around the distal portion of blade (700). Blade (700) further comprises opening (774), which may also be referred to herein as irrigation slot (774). Blade (700) further comprises micro slot (776) located in the tip of blade (700). In the present example, micro slot (774) has a width of about 0.005 inches. In other versions, the width of micro slot (774) can be greater or less than 0.005 inches. Micro slot (774) may be formed in blade (700) by machining the tip of blade (700) using electrical discharge machining (EDM) with a fine wire.

In bone cutting applications, the tip of blades not having micro slot (776) can be subject to excessive heat generation. This can occur when the tip is plunged within the bone and is blocked or inhibited from any cooling fluid that may be used. In the illustrated version, micro slot (776) connects the tip of blade (700) with irrigation slot (774). This allows for cooling fluid to pass through irrigation slot (774) to reach each side of blade (700), but also for cooling fluid to reach the tip of blade (700) and the cutting location even when the tip may be plunged within bone. With this configuration the tip of blade (700) can be cooled to counter excessive heat generation. Similarly, cooling fluid can be provided to the bone being cut by way of irrigation slot (774) and micro slot (776), which can aid in avoiding excessive bone heating and charring. Furthermore, cooling the tip of blade (700) using micro slot (776) may improve blade (700) stability and life since overheating the tip of blade (700) can lead to blade (700) failure.

By introducing micro slot (776), blade (700) also achieves increased flexibility. In this manner, with the inclusion of micro slot (776), the tip of blade (700) is divided into two portions. These two portions of the tip of blade (700) act to propagate the longitudinal wave, but additionally the lateral force imparted to blade (700) during cutting allows the two portions of the tip of blade (700) to translate laterally and in doing so to clear material out of micro slot (776). In some instances, irrigation can be used to further enhance clearing material from micro slot (776).

In the illustrated version, micro slot (776) is aligned with a longitudinal axis of blade (700) such that micro slot (776) bisects the tip of blade (770) in symmetrical manner. In this manner micro slot (776) extends parallel to irrigation slot (774). In another example, micro slot (776) may be offset from the longitudinal axis of blade (700). In view of the teachings herein, other ways to modify blade (700) having micro slot (776) will be apparent to those of ordinary skill in the art.

V. Exemplary Ultrasonic Surgical Instrument with Blade Having Chamfers and Rounded Distal End FIGS. 22-25 depict another exemplary ultrasonic blade (800) that may be incorporated into instrument (10) in place of blade (40). Alternatively, blade (800) may be incorporated into any other kind of ultrasonic surgical instrument, including instruments with or without liquid dispensing features like liquid dispensing feature (50). It should therefore be understood that blade (800) does not need to necessarily be used in conjunction with liquid cooling features, though blade (800) may be used with one or more liquid cooling features if desired.

Blade (800) of this example comprises body (802), irrigation slot (804), distal irrigation chamfers (822, 823), proximal irrigation chamfers (820, 821), top surface (810), bottom surface (811), side surfaces (814, 834), chamfered surfaces (812, 832, 842), and rounded distal end portions (852, 862). An additional chamfered surface (not shown) is below chamfer surface (832).

Blade (800) is symmetrical about its longitudinal axis. On a first side of blade (800), chamfered surface (812) and chamfered surface (842) converge to form one side edge of blade (800). Chamfered surface (812) terminates at top surface (810), while chamfered surface (842) terminates at bottom surface (811). On a second side of blade (800), chamfered surface (832) and another chamfered surface (not shown) converge to form a second side edge of blade (800). Chamfered surface (832) terminates at top surface (810), while the other chamfered surface (not shown) terminates at bottom surface (811). Adjacent to one side of chamfered surfaces (812, 832, 842) are rounded distal end portions (852, 862). Rounded distal end portion (852) is positioned along the top of blade (800), and rounded distal end portion (862) is positioned along the bottom of blade (800). Together, rounded distal end portions (852, 862) define a rounded nose. Adjacent to the opposite side of chamfered surfaces (812, 832, 842) are side surfaces (814, 834).

Figure 25:
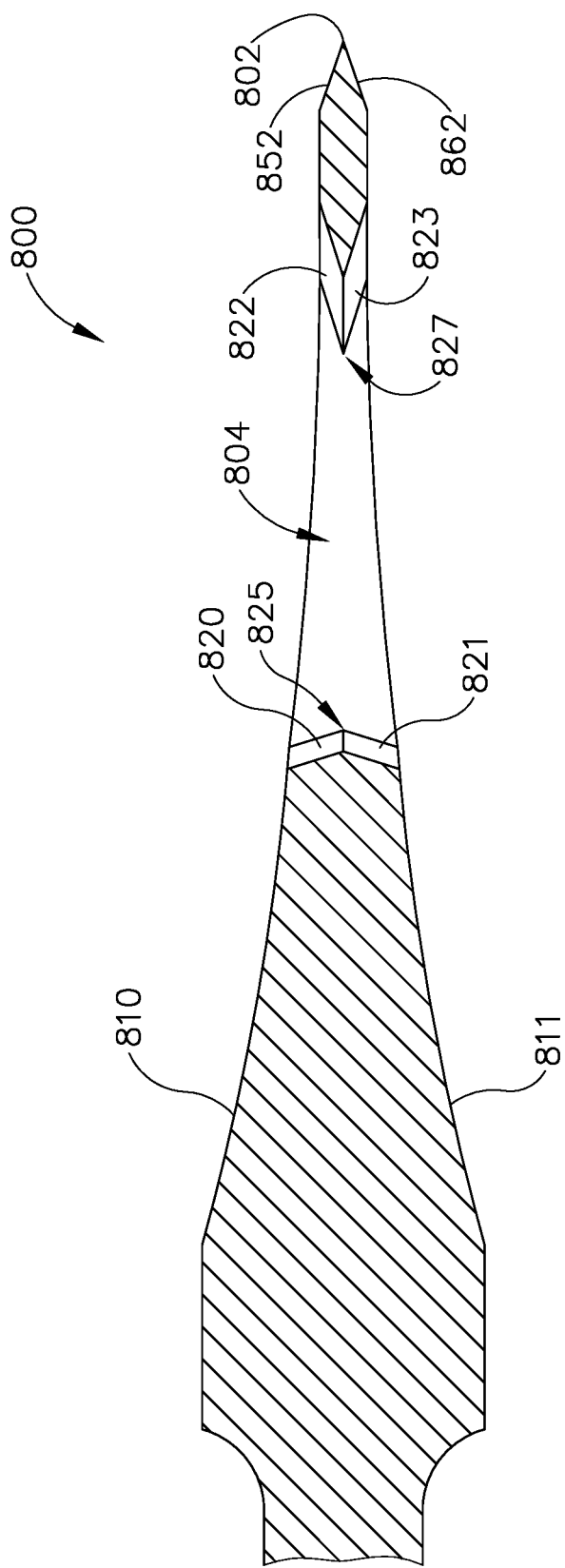
FIG. 25 depicts a cross-sectional view of the ultrasonic blade of FIG. 22, taken along line 25-25 of FIG. 24.

Extending between top surface (810) and bottom surface (811) is irrigation slot (804). As discussed above, irrigation slot (804) provides a path for cooling fluid to reach both sides of blade (800). In the present example irrigation slot (804) comprises distal irrigation chamfers (822, 823) and proximal irrigation chamfers (820, 821) as best seen in FIG. 25. When blade (800) is used with a cooling fluid, distal irrigation chamfers (822, 823) direct cooling fluid out from irrigation slot (804) to rounded distal end portions (852, 862). Similarly, proximal irrigation chamfers (820, 821) direct cooling fluid out from irrigation slot (804) proximally to respective top and bottom surfaces (810, 811) of blade (800). Referring to FIG. 25, distal irrigation chamfers (822, 823) converge to form peak (827). Similarly, proximal irrigation chamfers (820, 821) converge to form peak (825). Peaks (825, 827) each point towards a middle of irrigation slot (804), and in this manner peaks (825, 827) configured to promote directing cooling fluid from irrigation slot (804), up and out along irrigation chamfers (820, 821, 822, 823).

Top and bottom surfaces (810, 811) of blade (800) comprise a taper as top and bottom surfaces (810, 811) extend from the proximal region of blade (800) to the distal region of blade (800). In the present example, the taper can be characterized as exponential such that the taper decreases in an exponential fashion as top and bottom surfaces (810, 811) extend distally. With this configuration, a distal section of blade (800) is substantially straight, which may be useful in making plunge cuts with blade (800).

Figure 26:
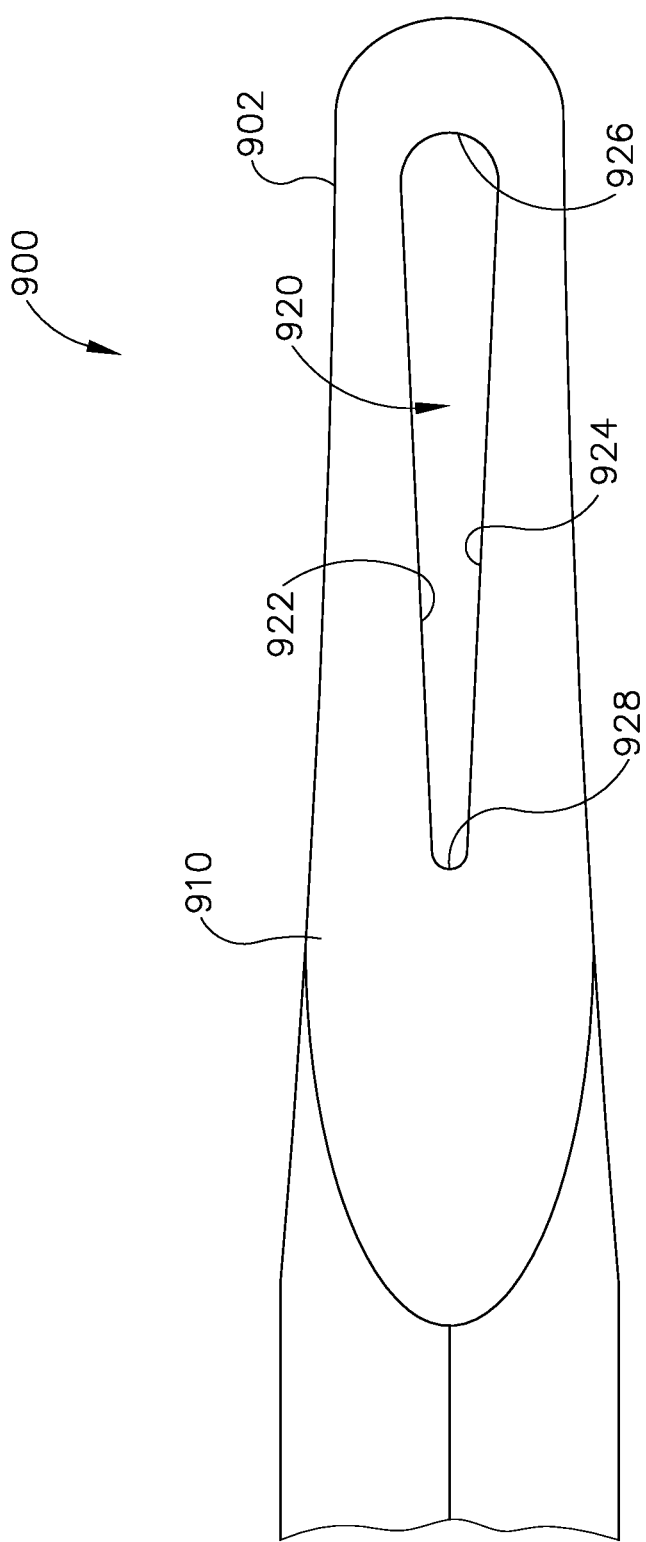
FIG. 26 depicts a top plan view of another exemplary ultrasonic blade that may be incorporated into the instrument of FIG. 1.

FIG. 26 depicts another exemplary ultrasonic blade (900) that may be incorporated into instrument (10) in place of blade (40). Alternatively, blade (900) may be incorporated into any other kind of ultrasonic surgical instrument, including instruments with or without liquid dispensing features like liquid dispensing feature (50). It should therefore be understood that blade (900) does not need to necessarily be used in conjunction with liquid cooling features, though blade (900) may be used with one or more liquid cooling features if desired.

Blade (900) of this example is similar to blade (800) and comprises body (902) similar to body (802) of blade (800). However, blade (900) comprises tear drop shaped irrigation slot (920). Irrigation slot (920) comprises proximal end (928), distal end (926), and sides (922, 924). Irrigation slot (920) extends through top surface (910) of blade (900) to the bottom surface (not shown). In the present example, the tear drop shape for irrigation slot (920) provides for less blade material generally, as well as specifically at the distal region of blade (900). In certain stress tests, a reduced amplitude drop-off has been observed where the amount of blade material is reduced, and such reduced amplitude drop-off corresponds with reduced stress measurements within the blade during use. In view of the teachings herein, other shapes and configurations for irrigation slots that may provide improved stress profiles will be apparent to those of ordinary skill in the art.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument comprising (a) a body; (b) an acoustic waveguide; (c) an ultrasonic blade positioned distally relative to the body, wherein the ultrasonic blade is in acoustic communication with the acoustic waveguide; (d) a first feature configured to mitigate excessive heat build-up, wherein the first feature comprises a liquid dispensing feature positioned distally relative to the body; and (e) a second feature configured to mitigate excessive heat build-up.

EXAMPLE 2

The surgical instrument of Example 1, wherein the liquid dispensing feature is positioned adjacent to the ultrasonic blade, wherein the liquid dispensing feature is configured to deliver a flow of cooling liquid to the ultrasonic blade.

EXAMPLE 3

The surgical instrument of any one or more of Examples 1 through 2, wherein the second feature comprises the ultrasonic blade having a serrated edge, wherein the serrated edge comprises a plurality of teeth.

EXAMPLE 4

The surgical instrument of Example 3, wherein the spacing between each of the plurality of teeth as measured by the spacing between a peak of a first tooth and an adjacent peak of a second tooth is in the range of about $\frac{1}{1000}$th to about $\frac{1}{10}$th of a harmonic wavelength for the acoustic waveguide.

EXAMPLE 5

The surgical instrument of any one or more of Examples 3 through 4, wherein the spacing between each of the plurality of teeth is in the range of about 0.004 inches to about 0.04 inches.

EXAMPLE 6

The surgical instrument of any one or more of Examples 3 through 5, wherein the serrated edge comprises a plurality of teeth having a pyramid shape.

EXAMPLE 7

The surgical instrument of any one or more of Examples 3 through 6, wherein the serrated edge comprises a plurality of teeth having a scalloped shape.

EXAMPLE 8

The surgical instrument of any one or more of Examples 3 through 7, wherein the serrated edge comprises a plurality of teeth having a triangular shape.

EXAMPLE 9

The surgical instrument of any one or more of Examples 3 through 8, wherein the plurality of teeth comprises first sloped surfaces and second sloped surfaces, wherein each of the first sloped surfaces defines a first angle with a longitudinal axis of the ultrasonic blade, and wherein each of the second sloped surfaces define a second angle with the longitudinal axis of the ultrasonic blade, wherein the first angle is an acute angle and is less than the second angle.

EXAMPLE 10

The surgical instrument of any Example 10, wherein the second angle is an obtuse angle.

EXAMPLE 11

The surgical instrument of Example 10, wherein the second angle is about a ninety-degree angle.

EXAMPLE 12

The surgical instrument of any one or more of Examples 3 through 11, wherein the ultrasonic blade defines a longitudinal axis, and wherein the plurality of teeth comprises first sloped surfaces and second sloped surfaces, wherein a first slope of each of first surfaces relative to the longitudinal axis is less than a second slope of each of second surfaces relative to the longitudinal axis.

EXAMPLE 13

The surgical instrument of any one or more of Examples 3 through 12, wherein each of the plurality of teeth comprises a peak, and wherein each of the plurality of teeth are not symmetrical about an axis extending through the peak orthogonally to a longitudinal axis defined by the ultrasonic blade.

EXAMPLE 14

The surgical instrument of any one or more of Examples 3 through 13, wherein the plurality of teeth comprises valleys, wherein the valleys are configured to receive the flow of cooling liquid from the liquid dispensing feature.

EXAMPLE 15

The surgical instrument of any one or more of Examples 1 through 14, wherein the second feature comprises the ultrasonic blade comprising (a) a distal end; (b) an irrigation slot fluidly connecting a first side of the blade with a second side of the blade; and (c) a micro slot extending through the distal end and connecting with the irrigation slot.

EXAMPLE 16

The surgical instrument of any one or more of Examples 1 through 15, wherein the second feature comprises an irrigation slot positioned within the ultrasonic blade and fluidly connecting a first side of the blade with a second side of the blade.

EXAMPLE 17

The surgical instrument Example 16, wherein the irrigation slot comprises at least one distal chamfer configured to direct cooling fluid from irrigation slot to a distal portion of the blade.

EXAMPLE 18

The surgical instrument of any one or more of Examples 16 through 17, wherein the irrigation slot comprises a tear drop shape.

EXAMPLE 19

An surgical instrument comprising (a) a body; (b) an acoustic waveguide; (c) an ultrasonic blade positioned distally relative to the body, wherein the ultrasonic blade is in acoustic communication with the acoustic waveguide; and (d) a liquid dispensing feature configured to mitigate excessive heat build-up, wherein the liquid dispensing feature comprises a lumen within the acoustic waveguide, wherein the lumen is configured to connect with a fluid source to deliver a flow of cooling liquid to the blade.

EXAMPLE 20

The surgical instrument of Example 19, wherein the lumen is positioned to direct the flow of cooling fluid onto one side of the blade.

EXAMPLE 21

The surgical instrument of Example 19, wherein the lumen is positioned to direct the flow of cooling fluid onto both sides of the blade.

EXAMPLE 22

The surgical instrument of any one or more of Examples 19 through 21, further comprising a pair of openings with one of the pair of openings on each side of the blade, wherein the pair of openings are in fluid communication with the lumen.

EXAMPLE 23

The surgical instrument of any one or more of Examples 19 through 22, further comprising multiple sets of openings with one of each of the multiple sets of openings positioned on each side of the blade, wherein the multiple sets of opening are in fluid communication with the lumen.

EXAMPLE 24

The surgical instrument of any one or more of Examples 19 through 23, wherein the ultrasonic blade comprises a lobe shape having a cutting edge defined by a pair of tapered surfaces.

EXAMPLE 25

The surgical instrument of any one or more of Examples 19 through 24, wherein at least one of the multiple sets of openings is configured to direct the flow of cooling fluid onto the cutting edge of the blade.

EXAMPLE 26

The surgical instrument of any one or more of Examples 19 through 25 in combination with the surgical instrument of any one or more of Examples 1 through 18.

EXAMPLE 27

A surgical instrument comprising (a) a body; (b) an acoustic waveguide; and (c) an ultrasonic blade positioned distally relative to the body, wherein the ultrasonic blade is in acoustic communication with the acoustic waveguide, wherein the ultrasonic blade comprises an oversize distal portion compared to a proximally adjacent portion of the blade.

EXAMPLE 28

The surgical instrument of Example 27, wherein the oversize distal portion is oversize in a first dimension coinciding with the thickness of the blade.

EXAMPLE 29

The surgical instrument of any one or more of Examples 27 through 28, wherein the oversize distal portion is oversize in a second dimension coinciding with the width of the blade.

EXAMPLE 30

The surgical instrument of any one or more of Examples 27 through 29, further comprising an irrigation slot.

EXAMPLE 31

The surgical instrument of any one or more of Examples 27 through 30, further comprising a transition region, wherein the blade thickness increases through the transition region as the blade extends distally.

EXAMPLE 32

The surgical instrument of any one or more of Examples 27 through 31 in combination with the surgical instrument of any one or more of Examples 1 through 26.

VII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising: (a) an acoustic waveguide extending along a longitudinal axis, wherein the acoustic waveguide defines a waveguide width transverse to the longitudinal axis; (b) an ultrasonic blade distally projecting relative to the acoustic waveguide and in acoustic communication with the acoustic waveguide, wherein the ultrasonic blade includes: (i) a blade body, (ii) a first side surface, (iii) a second side surface opposite the first side surface, and (iv) a cutting edge transversely between the first and second sides surfaces, wherein the cutting edge defines a cutting plane having a first side and a second side such that the first and second side surfaces are respectively positioned on the first and second sides of the cutting plane, wherein the blade body in the cutting plane defines a blade length along the longitudinal axis and a blade width transverse to the longitudinal axis, wherein the blade width is larger than the waveguide width, wherein the cutting edge is adjacent to the distal end of the acoustic waveguide, wherein the ultrasonic blade is offset from the longitudinal axis; and (c) a lumen extending at least partially through the acoustic waveguide and configured to connect with a fluid source to deliver a flow of cooling liquid to at least one of the first and second sides surfaces of the ultrasonic blade.

2. The surgical instrument of claim 1, wherein at least one of the first or second side surfaces is planar.

3. The surgical instrument of claim 2, wherein each of the first and second side surface is planar.

4. The surgical instrument of claim 1, wherein the ultrasonic blade further includes a first tapered surface and a second tapered surface, wherein the first and second tapered surfaces respectively extend from the first and second side surfaces together to define the cutting edge.

5. The surgical instrument of claim 1, wherein the acoustic waveguide defines the lumen and a distal opening in communication with the lumen.

6. The surgical instrument of claim 5, wherein the ultrasonic blade extends from the acoustic waveguide such that the distal opening is transversely positioned on only one of the first or second sides of the cutting plane.

7. The surgical instrument of claim 6, wherein the acoustic waveguide defines only one distal opening.

8. The surgical instrument of claim 1, wherein the cutting edge is continuous through the cutting plane.

9. The surgical instrument of claim 8, wherein the blade body defines a perimeter, and wherein the cutting edge extends continuously about at least a majority of the perimeter.

10. The surgical instrument of claim 1, further comprising:
    (a) a body, wherein the ultrasonic blade distally projects relative to the body; and
    (b) a port fluidly connected to the lumen and configured to connect to the fluid source for communicating the flow of cooling liquid therealong.

11. The surgical instrument of claim 1, wherein the blade body has a lobe shape or a disc shape.

12. The surgical instrument of claim 1, wherein the acoustic waveguide extends along the longitudinal axis to a distal end, wherein the distal end faces distally and defines a distal opening, wherein the lumen is fluidly connected to the distal opening, and wherein the distal opening distally faces toward the ultrasonic blade and the lumen is configured to connect with the fluid source to deliver the flow of cooling liquid to at least one of the first and second sides surfaces of the ultrasonic blade.

13. The surgical instrument of claim 1, wherein the blade body has a disc shape.

14. A method of cooling an ultrasonic blade of an surgical instrument, the surgical instrument including (a) an acoustic waveguide extending along a longitudinal axis, wherein the acoustic waveguide defines a waveguide width transverse to the longitudinal axis; (b) the ultrasonic blade distally projecting relative to the acoustic waveguide and in acoustic communication with the acoustic waveguide, wherein the ultrasonic blade includes: (i) a blade body, (ii) a first side surface, (iii) a second side surface opposite the first side surface, and (iv) a cutting edge transversely between the first and second sides surfaces, wherein the cutting edge defines a cutting plane having a first side and a second side such that the first and second side surfaces are respectively positioned on the first and second sides of the cutting plane, wherein the blade body in the cutting plane defines a blade length along the longitudinal axis and a blade width transverse to the longitudinal axis, wherein the blade width is larger than the waveguide width, wherein the cutting edge is adjacent to the distal end of the acoustic waveguide, wherein the ultrasonic blade is offset from the longitudinal axis; and (c) a lumen extending at least partially through the acoustic waveguide and configured to connect with a fluid source to deliver a flow of cooling liquid to at least one of the first and second sides surfaces of the ultrasonic blade, the method comprising: (a) expelling a flow of cooling liquid from a distal opening; and (b) delivering the flow of cooling liquid to at least one of the first and second sides surfaces of the ultrasonic blade.

15. The method of claim 14, wherein the acoustic waveguide defines the lumen and the distal opening in communication with the lumen, wherein the ultrasonic blade extends from the acoustic waveguide such that the distal opening is transversely positioned on only one of the first or second sides of the cutting plane, and wherein the method further includes: (a) initially contacting the flow of cooling liquid to the first side surface of the ultrasonic blade, and (b) distributing the flow of cooling liquid from the first side surface to a tissue.

16. A surgical instrument, comprising:
- (a) an acoustic waveguide extending along a longitudinal axis to a distal end, wherein the distal end faces distally and defines a distal opening;
- (b) an ultrasonic blade distally extending from the distal end of the acoustic waveguide and in acoustic communication with the acoustic waveguide, wherein the ultrasonic blade includes:
  - (i) a blade body,
  - (ii) a first side surface,
  - (iii) a second side surface opposite the first side surface, and
  - (iv) a cutting edge transversely between the first and second sides surfaces, wherein the cutting edge defines a cutting plane having a first side and a second side such that the first and second side surfaces are respectively positioned on the first and second sides of the cutting plane; and
- (c) a lumen in fluid communication with the distal opening such that the lumen extends at least partially through the acoustic waveguide and distally terminates at the distal opening defined by the distal end of the acoustic waveguide with the ultrasonic blade extending therefrom, wherein the distal opening distally faces toward the ultrasonic blade and the lumen is configured to connect with a fluid source, and wherein the distal opening is configured to deliver a flow of cooling liquid therefrom to at least one of the first and second sides surfaces of the ultrasonic blade.

17. The surgical instrument of 16, wherein the distal opening is positioned on the longitudinal axis.

* * * * *